(12) United States Patent
Shimizu et al.

(10) Patent No.: US 11,389,381 B2
(45) Date of Patent: Jul. 19, 2022

(54) COSMETIC SOLID COMPOSITION COMPRISING A NON VOLATILE HYDROCARBONATED OIL, WAXES AND A HIGH CONTENT FROM NON VOLATILE PHENYLATED SILICONE OIL

(71) Applicants: Momoko Shimizu, Tokyo (JP); Maki Ishida, Asaka (JP)

(72) Inventors: Momoko Shimizu, Tokyo (JP); Maki Ishida, Asaka (JP)

(73) Assignee: L'OREAL, Paris (FR)

( * ) Notice: Subject to any disclaimer, the term of this patent is extended or adjusted under 35 U.S.C. 154(b) by 328 days.

(21) Appl. No.: 14/409,146

(22) PCT Filed: Jun. 21, 2013

(86) PCT No.: PCT/JP2013/067742
§ 371 (c)(1),
(2) Date: Dec. 18, 2014

(87) PCT Pub. No.: WO2013/191300
PCT Pub. Date: Dec. 27, 2013

(65) Prior Publication Data
US 2015/0320673 A1 Nov. 12, 2015

(30) Foreign Application Priority Data
Jun. 21, 2012 (WO) .................. PCT/JP2012/066453

(51) Int. Cl.
| | | |
|---|---|---|
| *A61K 8/31* | (2006.01) | |
| *A61Q 1/06* | (2006.01) | |
| *A61K 8/81* | (2006.01) | |
| *A61K 8/891* | (2006.01) | |

(52) U.S. Cl.
CPC .............. *A61K 8/31* (2013.01); *A61K 8/8111* (2013.01); *A61K 8/891* (2013.01); *A61Q 1/06* (2013.01); *A61K 2800/30* (2013.01); *A61K 2800/43* (2013.01); *A61K 2800/5922* (2013.01)

(58) Field of Classification Search
CPC .............. A61K 8/31; A61K 8/891; A61Q 1/06
See application file for complete search history.

(56) References Cited

U.S. PATENT DOCUMENTS

| | | | |
|---|---|---|---|
| 5,750,723 A | 5/1998 | Eldin et al. | |
| 5,847,156 A | 12/1998 | Eldin et al. | |
| 5,965,148 A | 10/1999 | Agostini et al. | |
| 6,048,918 A | 4/2000 | Eldin et al. | |
| 6,136,332 A | 10/2000 | Grollier et al. | |
| 6,491,927 B1 | 12/2002 | Arnau et al. | |
| 7,470,725 B2 | 12/2008 | Schwertfeger et al. | |
| 2001/0031269 A1* | 10/2001 | Arnaud .................. | A61K 8/891 424/401 |
| 2004/0151680 A1* | 8/2004 | Patil ....................... | A61K 8/891 424/70.12 |
| 2005/0245673 A1 | 11/2005 | Ferrari et al. | |
| 2007/0092462 A1 | 4/2007 | Gans Russ et al. | |
| 2008/0171006 A1 | 7/2008 | Bui et al. | |
| 2008/0233064 A1 | 9/2008 | Tabakman et al. | |
| 2009/0247648 A1 | 10/2009 | Zhao | |
| 2011/0142774 A1 | 6/2011 | Tomita et al. | |
| 2012/0171138 A1* | 7/2012 | Bradshaw .............. | A61K 8/898 424/64 |
| 2012/0237467 A1* | 9/2012 | Sasada .................... | A61K 8/31 424/64 |

FOREIGN PATENT DOCUMENTS

| | | |
|---|---|---|
| EP | 0542669 A1 | 5/1993 |
| EP | 0787730 A1 | 8/1997 |
| EP | 0787731 A2 | 8/1997 |
| EP | 0847752 A1 | 6/1998 |
| EP | 0955039 A1 | 11/1999 |
| FR | 2792190 A1 | 10/2000 |
| FR | 2892929 A1 | 5/2007 |
| FR | 2943245 A1 | 9/2010 |
| FR | 2945941 A1 | 12/2010 |
| FR | 2945942 A1 | 12/2010 |
| JP | 2011-140481 A | 7/2011 |
| JP | 2012-082188 A | 4/2012 |
| JP | 2012-149040 A | 8/2012 |
| JP | 2012-250927 A | 12/2012 |
| KR | 2012-0062938 A | 6/2012 |
| WO | 96/08537 A1 | 3/1996 |
| WO | 03/061612 A1 | 7/2003 |
| WO | 2006/028265 A1 | 3/2006 |
| WO | 2009/150852 A1 | 12/2009 |
| WO | WO-2011065101 A1 * | 6/2011 ............... A61K 8/31 |

OTHER PUBLICATIONS

Espacenet machine English translation of WO 2011/065101 A1.*
A. Foxon-Hill, "The Lipstick Chronicals: What makes some lipsticks stick for up to 12 hours?" <https://realizebeauty.wordpress.com/2009/07/06/the-lipstick-chronicals-what-makes-some-lipsticks-stick-for-up-to-12-hours/>, published Jul. 6, 2009, p. 1-3.*
International Search Report and Written Opinion for PCT/JP2013/067742, dated Sep. 13, 2013.
English language abstract for FR 2892929 (May 11, 2007).
English language abstract for FR 2943245 (Sep. 24, 2010).
English language abstract for FR 2945941 (Dec. 3, 2010).
English language abstract for FR 2945942 (Dec. 3, 2010).
English language abstract for EP 0847752 (Jun. 17, 1998).
English language abstract for FR 2792190 (Oct. 20, 2000).

(Continued)

*Primary Examiner* — Nannette Holloman
(74) *Attorney, Agent, or Firm* — The Marbury Law Group, PLLC

(57) ABSTRACT

The present invention relates to solid compositions for making up and/or caring for the skin and/or the lips, comprising at least one fatty phase comprising: —from 5 to 30% by weight of non volatile hydrocarbonated apolar oil(s), or mixture thereof, relative to the total weight of the composition, —from 43 to 90% by weight of total content of non volatile silicone oil(s) relative to the total weight of the composition, wherein at least one of said non volatile silicone oil(s) is a non volatile phenylated silicon oil, and— from 3 to 30% by weight of wax(es), or mixture thereof, relative to the total weight of the composition.

17 Claims, No Drawings

(56) References Cited

OTHER PUBLICATIONS

Van de Hulst, H.C., "Light Scattering by Small Particles," Chapters 9 and 10, Wiley, NY, 1957.
Japanese Office Action for counterpart Application No. JP2014-560170, dated Mar. 6, 2017, with English translation.
European Patent Office Action for copending EP Application No. 13737871.7, dated Dec. 12, 2018.
Translated Decision to Grant for counterpart KR Application No. 10-2014-7033272, dated Apr. 29, 2020.
Mintel: "Curvy Lip Liquid," Makemania, Record ID 960364, Aug. 2008.
Non-Final Office Action for copending U.S. Appl. No. 17/339,455, dated Apr. 1, 2022.

\* cited by examiner

COSMETIC SOLID COMPOSITION COMPRISING A NON VOLATILE HYDROCARBONATED OIL, WAXES AND A HIGH CONTENT FROM NON VOLATILE PHENYLATED SILICONE OIL

CROSS REFERENCE TO RELATED APPLICATIONS

This is a national stage application of PCT/JP2013/067742, filed internationally on Jun. 21, 2013, which claims priority to PCT/JP2012/066453, filed Jun. 21, 2012.

TECHNICAL FIELD

The present invention relates to a cosmetic composition, more particularly to a cosmetic composition for making up and/or caring for the skin and/or the lips, comprising a high content of non volatile silicone oil(s), wherein at least one oil is a non volatile phenylated silicone oil, a non volatile hydrocarbonated apolar oil, and waxes in a particular content.

The present invention also relates to the processes using such composition for making up and/or caring for the skin and/or the lips, comprising the application to the skin and/or the lips of such cosmetic composition.

BACKGROUND ART

In general, when women use a makeup product, especially of lips products such as lipstick or lipgloss type, they wish this product to have, after application, comfort and good remanence on the skin or the lips, in particular not to be transferred, and in particular no color or a low level of color to be transferred. Moreover, the product has to be easy to apply and the deposit has to be shiny.

However, in the past, it has been difficult to achieve composition that are homogenous and stable, and that enable the obtention of a shiny deposit having a good color transfer resistance level. Therefore, it is sought to further improve the cosmetic properties of the said compositions, in particular the applications properties such as the glide and the easiness to apply (easiness of the erosion of the composition in case of a solid composition) and to obtain a uniform (homogenous) deposit on the lips and/or the skin, and in particular to have a deposit on the skin and/or the lips that has a good transfer resistance, and in particular a good color transfer resistance. The deposit should also be shiny and/or sparingly tacky or not tacky and have a good shine level.

DISCLOSURE OF INVENTION

The inventors have found, unexpectedly, that it turns out to be possible to overcome this drawback provided that at least a non volatile apolar hydrocarbon-based oil, a non volatile dimethicone oil and a non volatile phenylated silicone oil are used in combination in a particular content, preferably in a solid composition.

The aim of the present invention is to overcome these drawbacks and to propose a cosmetic composition that is homogenous, stable (for example no separation into two phases, and/or exudation, and/or sedimentation of the pigments), and capable, in particular to form a deposit (particularly on the lips) that has a satisfying color transfer resistance level, and at the same time, capable of affording good cosmetic properties; in particular applications properties such as glide and easiness to apply, in particular on the lips, and forming a deposit having at least an acceptable level of shine (moderately good, good or very good level of shine). More preferably, the composition according to the invention should be stable after 72 hours at room temperature. Thus, according to one of its aspects, the invention relates to a solid cosmetic composition for making up and/or caring for the skin and/or the lips, comprising in a physiologically acceptable medium, at least one fatty phase comprising:

- from 5 to 30% by weight of non volatile hydrocarbonated apolar oil(s), or mixture thereof, relative to the total weight of the composition,
- from 43 to 90% by weight of total content of non volatile silicone oil(s), preferably between 45 and 70% by weight, relative to the total weight of the composition, wherein at least one of said non volatile silicone oil(s) is a non volatile phenylated silicon oil, and
- from 3 to 30% by weight of wax(es), or mixture thereof, relative to the total weight of the composition.

Such a composition is stable and homogenous, and are preferably makeup compositions, whose deposition on keratin materials, and in particular the lips and/or the skin, is easy to apply (good glide, homogenous deposit) and the deposit has good transfer resistance after application (in particular a satisfactory color transfer resistance level (no transfer or poor transfer of the color of the deposit), in particular on a cup or a glass while drinking for example). Beside, the deposit obtained with such composition, is sparingly tacky or non-tacky, and has a sufficient level of shine (moderately good to very good).

The present invention also relates to a cosmetic process for making up and/or caring for the skin and/or the lips, comprising at least the application to the said skin and/or the said lips of a solid composition comprising, in a physiologically acceptable medium, at least one fatty phase comprising:

- from 5 to 30% by weight of non volatile hydrocarbonated apolar oil(s), or mixture thereof; relative to the total weight of the composition,
- from 43 to 90% by weight of total content of non volatile silicone oil(s), preferably between 45 and 70% by weight relative to the total weight of the composition, wherein at least one of said non volatile silicone oil(s) is a non volatile phenylated silicon oil, and
- from 3 to 30% by weight of wax(es), or mixture thereof; relative to the total weight of the composition.

BEST MODE FOR CARRYING OUT THE INVENTION

Advantageously, the composition under consideration according to the invention is an oil-in-oil type composition. In the oil in oil type cosmetic composition of the invention, the non volatile silicone oil(s) and the non volatile hydrocarbon oil(s) are in a stable oil in oil state before application, without being separated from each other. After application, the non volatile silicone oil comes up to the surface of the deposit, and this separated non volatile silicone oil covers an adherent layer of the non volatile hydrocarbonated oil. Therefore, the resulting composition has good transfer resistance (in particular color transfer resistance) and offers a good level of shine. Rubbing the lips again each other during application further enhance this separation.

Advantageously, the composition under consideration according to the invention is anhydrous.

Physiologically Acceptable Medium

For the purposes of the present invention, the term "physiologically acceptable medium" is intended to denote a medium that is suitable for the application of a composition to the skin and/or the lips, for instance the oils or organic solvents commonly used in cosmetic compositions.

The physiologically acceptable medium (acceptable tolerance, toxicology and feel) is generally adapted to the nature of the support onto which the composition is to be applied, and also to the form in which the composition is to be conditioned.

As emerges from the examples below, the combination under consideration according to the invention proves to be most particularly effective for affording a composition whose deposit on the skin or the lips that simultaneously has improved gloss and non transfer properties. Beside, the deposit also exhibit remanence over time, in particular of remanence of the colour of the deposit (no embrittlement or fragmentation of the deposit, which remains homogeneous) and satisfactory comfort properties, both on application (especially glidance, breakdown, thickness and uniformity of the deposit formed, and reduction of the tack on drying) and during wearing, namely softness, absence of a tacky sensation or of a sensation of tautness or dryness.

What is more, in the case of lipsticks (solid), this improvement of non transfer and non tackiness or sparingly tackiness is not obtained at the expense of the shine, which is another property generally sought for a makeup product of this type. Specifically, contrary to all expectation, no matt effect of the cosmetic product containing the combination under consideration according to the invention is noted.

The invention also preferably relates to a solid composition for making up and/or caring for the skin and/or the lips, comprising, in a physiologically acceptable medium,
- from 5 to 30% by weight of non volatile hydrocarbonated apolar oil(s), or mixture thereof, relative to the total weight of the composition,
- from 43 to 90% by weight of total content of non volatile silicone oil(s), preferably between 45 and 70% by weight, relative to the total weight of the composition, wherein at least one of said non volatile silicone oil(s) is a non volatile phenylated silicon oil, and
- from 3 to 30% by weight of wax(es), or mixture thereof, relative to the total weight of the composition, and
- at least one colouring agent.

According to one preferred embodiment, in particular in the case of a composition intended for caring for and/or making up the lips, the composition used according to the invention is anhydrous or contains less than 3% by weight of water and preferably less than 1% by weight of water, relative to the total weight of the composition.

The term "anhydrous" especially means that water is preferably not deliberately added to the composition, but may be present in trace amount in the various compounds used in the composition.

The composition according to the invention and/or that used according to the process according to the invention may be in the form of a composition for making up the skin and/or the lips, especially for facial or bodily skin; it may be a complexion product such as a foundation, a face powder or an eyeshadow; a lip product such as a lipstick or a lipcare product; a concealer product; a blusher; an eyeliner; a lip pencil or an eye pencil; a body makeup product.

According to a first advantageous embodiment of the invention, the composition is a lip product such as a lipstick, a lipcare product or a lip pencil, and more preferably the composition is intended for making up the lips and it is more particularly a lipstick (lipstick wand).

Advantageously, the lipstick compositions according to the invention are anhydrous.

The compositions under consideration according to the invention and used in the processes according to the invention are in solid form at 20° C.

For the purposes of the invention, the term "solid" characterizes the state of the composition at a temperature of 20° C. In particular, a solid composition according to the invention has, at a temperature of 20° C. and at atmospheric pressure (760 mmHg), a hardness of greater than 30 $Nm^{-1}$ and preferably greater than 35 $Nm^{-1}$.

Protocol for Measuring the Hardness:

The hardness of a composition especially of lipstick wand type is measured according to the following protocol:

The stick of lipstick is stored at 20° C. for 24 hours before measuring the hardness.

The hardness may be measured at 20° C. via the "cheese wire" method, which consists in transversely cutting a wand of product, which is preferably a circular cylinder, by means of a rigid tungsten wire 250 μm in diameter, by moving the wire relative to the stick at a speed of 100 mm/minute.

The hardness of the samples of compositions of the invention, expressed in $Nm^{-1}$, is measured using a DFGS2 tensile testing machine from the company Indelco-Chatillon.

The measurement is repeated three times and then averaged. The average of the three values read using the tensile testing machine mentioned above, noted Y, is given in grams. This average is converted into newtons and then divided by L which represents the longest distance through which the wire passes. In the case of a cylindrical wand, L is equal to the diameter (in metres).

The hardness is converted into $Nm^{-1}$ by the equation below:

$$(Y \times 10^{-3} \times 9.8)/L$$

For a measurement at a different temperature, the stick is stored for 24 hours at this new temperature before the measurement.

According to this measuring method, a solid composition according to the invention has a hardness at 20° C. of greater than or equal to 30 $Nm^{-1}$, preferably greater than 35 $Nm^{-1}$ and preferably greater than 40 $Nm^{-1}$.

Preferably, the composition according to the invention especially has a hardness at 20° C. of less than 500 $Nm^{-1}$, especially less than 400 $Nm^{-1}$ and preferably less than 300 $Nm^{-1}$.

In particular, a composition whose hardness is greater than 30 $Nm^{-1}$ is said to be "solid" at 20° C. and at atmospheric pressure (760 mmHg).

Preferably, the composition according to the invention especially has a hardness value at 20° C. comprised between 40 $Nm^{-1}$ and 200 $Nm^{-1}$.

Preferably the hardness is comprised between 50 $Nm^{-1}$ and 200 $Nm^{-1}$, preferably between 60 $Nm^{-1}$ and 200 $Nm^{-1}$.

The terms "between" and "ranging from" should be understood as including the limits.

The example that follows is given as an illustration, without any limiting nature.

The present invention also covers a cosmetic process for making up and/or caring for the lips, comprising at least the application to the said lips of a composition as defined above.

Fatty Phase

The composition according to the invention comprises at least one fatty phase and more particularly at least one liquid fatty phase.

Non Volatile Silicone Oil

The composition according to the invention comprises at least a non volatile silicone oil. More particularly, the composition according to the invention comprises at least a non volatile phenylated silicone oil.

The composition according to the invention comprises from 43 to 90% by weight of total content of non volatile silicone oil(s), or mixture thereof, preferably between 45 and 70% by weight, relative to the total weight of the composition, wherein at least one of said non volatile silicone oil(s) is a non volatile phenylated silicon oil.

Preferably the composition according to the invention comprises from 43 to 90% by weight of total content of non volatile phenylated silicone oil(s), or mixture thereof, preferably between 45 and 70% by weight, relative to the total weight of the composition.

If the composition comprises non volatile silicone oil(s) having at least a dimethicone part, then according to a preferred embodiment of the present invention, the weight ratio of the non volatile phenylated silicone oil(s) having at least a dimethicone part on the non volatile phenylated silicone oil(s) with no dimethicone part is below 0.02, preferably below 0.01.

But preferably, according to this embodiment, said non volatile phenylated silicone oil(s) has no dimethicone part.

More particularly, the composition according to the invention, comprise from 45% to 70% by weight of total content of non volatile silicone oil(s), preferably between 50 and 70% by weight, relative to the total weight of the composition, wherein at least one of said non volatile silicone oil(s) is a non volatile phenylated silicon oil, relative to the total weight of the composition.

More preferably, the composition according to the invention, comprise from 45% to 70% by weight of total content of non volatile phenylated silicone oil(s), preferably between 50 and 70% by weight, relative to the total weight of the composition, relative to the total weight of the composition.

According to one particular embodiment, especially in the case of a lip makeup composition (lipstick), it may comprise from 45% to 70% by weight of non volatile phenylated silicone oil(s) according to the invention relative to the total weight of the composition.

If the composition comprises non volatile silicone oil(s) having at least a dimethicone part, then according to a preferred embodiment of the present invention, the weight ratio of the non volatile phenylated silicone oil(s) having at least a dimethicone part on the non volatile phenylated silicone oil(s) with no dimethicone part is below 0.02, preferably below 0.01.

Preferably according to this embodiment, said non volatile phenylated silicone oil(s) has no dimethicone part.

According to a preferred embodiment, the composition according to the invention is free of non volatile phenylated silicone oil(s) having at least a dimethicone part. This embodiment exhibit particular advantages regarding the homogeneity and the stability of the composition, as well as of the deposit on the skin and/or the lips.

According to a preferred embodiment, the composition according to the invention is free of non volatile silicone oil(s) having at least a dimethicone part.

The term "oil" means a water-immiscible non-aqueous compound that is liquid at room temperature (25° C.) and at atmospheric pressure (760 mmHg).

The silicone oils that may be used according to the invention are non-volatile.

In particular, the non-volatile silicone oils that may be used in the invention preferably have a viscosity at 25° C. comprised between 9 cSt and 800 000 cSt, preferably less than or equal to 600 000 cSt and preferably less than or equal to 500 000 cSt. The viscosity of these silicone oils may be measured according to standard ASTM D-445.

The term "non-volatile oil" means an oil whose vapour pressure at room temperature and atmospheric pressure is non-zero and less than 0.02 mmHg (2.66 Pa) and better still less than $10^{-3}$ mmHg (0.13 Pa). The non-volatile silicone oil that may be used in the invention may be chosen especially from silicone oils especially with a viscosity at 25° C. of greater than or equal to 9 centistokes (cSt) ($9 \times 10^{-6}$ m$^2$/s) and preferably less than 800 000 cSt, preferably between 50 and 600 000 cSt and preferably between 100 and 500 000 cSt. The viscosity of this silicone oil may be measured according to standard ASTM D -445.

Among these silicone oils, two types of oil may be distinguished, according to whether or not they contain phenyl.

1. Non Volatile Phenylated Silicone Oil:

A composition according to the invention contains at least one non-volatile phenylated silicone oil.

The expression "phenylated silicone oil" or "phenyl silicone oil" means a silicone oil having at least one phenyl substituent.

Moreover, the phenylated silicone oil(s) may have at least a dimethicone part or not.

It has to be noted that if the composition comprises non volatile silicone oil(s) having at least a dimethicone part, then according to a preferred embodiment of the present invention, the weight ratio of the non volatile phenylated silicone oil(s) having at least a dimethicone part on the non volatile phenylated silicone oil(s) with no dimethicone part is below 0.02, preferably below 0.01. Preferably, the non volatile phenylated silicone oil(s) have no dimethicone part.

Preferably, the composition according to the invention comprises from 10% to 90% by total weight of total content of non volatile phenylated silicone oil(s), preferably between 20 and 70% by weight, or mixture thereof relative to the total weight of the composition.

Preferably, the composition according to the invention comprises from 30% to 60% by total weight of total content of non volatile phenylated silicone oil(s), or mixture thereof relative to the total weight of the composition.

According to a particular embodiment, the composition according to the invention comprises from 43 to 90% by weight of total content of non volatile phenylated silicone oil(s), or mixture thereof, preferably between 45 and 70% by weight, relative to the total weight of the composition. According to this embodiment, the composition may be free from non volatile non phenylated silicone oil.

More particularly, the composition according to the invention, comprise from 45% to 70% by weight of total content of non volatile silicone oil(s), preferably between 50 and 70% by weight, relative to the total weight of the composition, wherein at least one of said non volatile silicone oil(s) is a non volatile phenylated silicon oil, relative to the total weight of the composition. The non volatile phenylated silicone oil may be chosen from:

a) the phenyl silicone oils corresponding to the following formula (I):

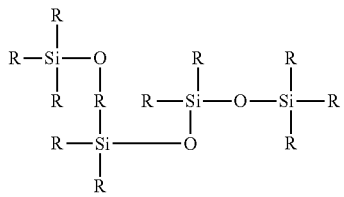

in which the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

b) the phenyl silicone oils corresponding to the following formula (II):

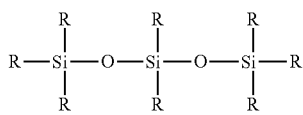

in which the groups R represent, independently of each other, a methyl or a phenyl, with the proviso that at least one group R represents a phenyl. Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes.

c) the phenyl silicone oils corresponding to the following formula (III):

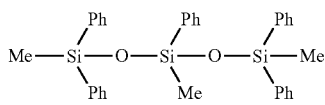

in which Me represents methyl, Ph represents phenyl.

Such a phenyl silicone oil is preferably trimethyl pentaphenyl trisiloxane, or Tetramethyl Tetraphenyl Trisiloxane.

Such oils are especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane), or Tetramethyl Tetraphenyl Trisiloxane sold under the reference Dow Corning 554 Cosmetic Fluid by Dow Corning may also be used.

d) the phenyl silicone oils corresponding to the following formula (IV):

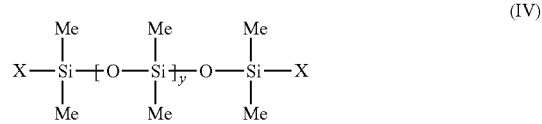

in which Me represents methyl, y is between 1 and 1,000 and X represents —$CH_2$—$CH(CH_3)(Ph)$.

e) the phenyl silicone oils corresponding to formula (V) below:

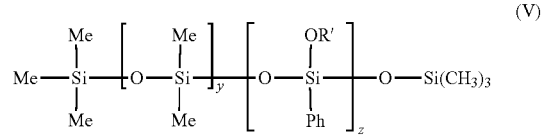

in which Me is methyl and Ph is phenyl, OR' represents a group —$OSiMe_3$ and y is 0 or ranges between 1 and 1000, and z ranges between 1 and 1000. In particular, y and z are such that compound (V) is a non-volatile oil.

According to a first embodiment, y ranges between 1 and 1000. Use may be made, for example, of trimethyl siloxyphenyl dimethicone, sold especially under the reference Belsil PDM 1000 sold by the company Wacker.

According to a second embodiment, y is equal to 0. Use may be made, for example, of phenyl trimethylsiloxy trisiloxane, sold especially under the reference Dow Corning 556 Cosmetic Grade Fluid (DC556), f) the phenyl silicone oils corresponding to formula (VI) below, and mixtures thereof:

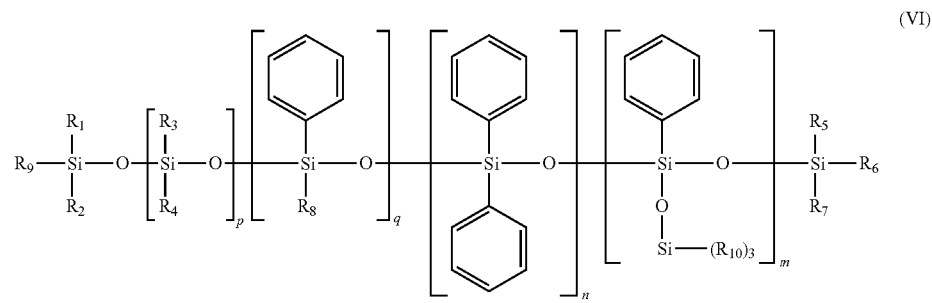

in which:
- $R_1$ to $R_{10}$, independently of each other, are saturated or unsaturated, linear, cyclic or branched $C_1$-$C_{30}$ hydrocarbon-based radicals,
- m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

Preferably, $R_1$ to $R_{10}$, independently of each other, represent a saturated or unsaturated linear or branched $C_1$-$C_{30}$, hydrocarbon radical, preferably saturated, and especially $C_1$-$C_{12}$ hydrocarbon-based radical, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical. Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may especially be identical, and in addition may be a methyl radical.

g) the phenyl silicone oils corresponding to formula (VII) below, and mixtures thereof:

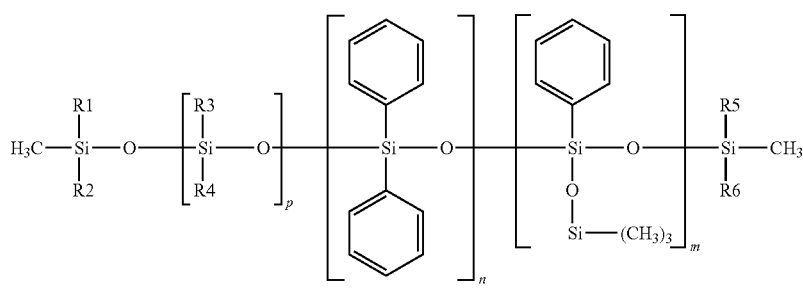

(VII)

in which:
- $R_1$ to $R_6$, independently of each other, are saturated or unsaturated, linear, cyclic or branched $C_1$-$C_{30}$ hydrocarbon-based radicals, preferably $R_1$ to $R_6$ are a $C_1$-$C_{30}$ alkyl radical, an aryl radical or an aralkyl radical
- m, n and p are, independently of each other, integers between 0 and 100, with the proviso that the sum n+m is between 1 and 100.

Preferably, $R_1$ to $R_6$, independently of each other, represent a saturated or unsaturated linear or branched $C_1$-$C_{30}$, hydrocarbon radical, preferably saturated, and especially $C_1$-$C_{12}$ hydrocarbon-based radical, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical. Preferably, $R_1$ to $R_6$ may each represent a methyl, ethyl, propyl, butyl, isopropyl, decyl, dodecyl or octadecyl radical, or alternatively a phenyl, tolyl, benzyl or phenethyl radical.

$R_1$ to $R_6$ may especially be identical, and in addition may be a methyl radical. Preferably, m=1 or 2 or 3, and/or n=0 and/or p=0 or 1 may apply, in formula (VII).

h) the phenyl silicone oils corresponding to the following formula, and mixtures thereof:

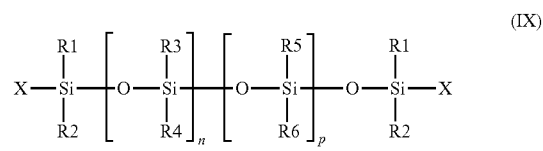

(IX)

in which:
- $R_1$, $R_2$, $R_5$ and $R_6$ are, together or separately, an alkyl radical containing 1 to 6 carbon atoms,
- $R_3$ and $R_4$ are, together or separately, an alkyl radical containing from 1 to 6 carbon atoms or an aryl radical, with the proviso that at least one from $R_3$ and $R_4$ is a phenyl radical,
- X is an alkyl radical containing from 1 to 6 carbon atoms, a hydroxyl radical or a vinyl radical,
- n and p being integer superior or equal to 1, chosen so as to give the oil a weight-average molecular mass of less than 200 000 g/mol, preferably less than 150 000 g/mol and more preferably less than 100 000 g/mol.

i) and mixture thereof.

As preferred non-volatile silicone oils, examples that may be mentioned include silicone oils such as:
- phenyl silicone oil, preferably chosen from: Tetramethyl Tetraphenyl Trisiloxane (such as as PH-1554 HRI or Dow Corning 554 Cosmetic Fluid from Dow Corning), trimethylsiloxyphenyldimethicone (for instance Belsil PDM 1000 from the company Wacker (cf. formula (V) above)), phenyl trimethicones (such as the phenyl trimethicone sold under the trade name DC556 by Dow Corning), phenyl dimethicones, phenyltrimethylsiloxydiphenylsiloxanes, diphenyl dimethicones (such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt), diphenylmethyldiphenyltrisiloxanes, 2-phenylethyl trimethylsiloxysilicates, trimethylpentaphenyl trisiloxane (such as the product sold under the name Dow Corning PH-1555 HRI Cosmetic fluid by Dow Corning) (cf. formula (III) above), diphenylsiloxy phenyltrimethicone (such as KF56 A from Shin Etsu),
- non-volatile polydimethylsiloxanes (PDMS), polydimethylsiloxanes comprising alkyl or alkoxy groups, which are pendent and/or at the end of the silicone chain, these groups each containing from 2 to 24 carbon atoms, and
- mixtures thereof.

The phenyl silicones are more preferably chosen from:
- phenyl trimethicones,
- Tetramethyl Tetraphenyl Trisiloxane,
- diphenylsiloxyphenyltrimethicone, diphenylsiloxyphenyldimethicone,
trimethylpentaphenyl trisiloxane,
phenyldimethicones,
phenyltrimethylsiloxydiphenylsiloxanes,
diphenyl dimethicones,
diphenylmethyldiphenyltrisiloxanes and
2-phenylethyl trimethylsiloxysilicates, and
mixtures thereof.

More particularly, the phenyl silicones are chosen from:
phenyl trimethicones,
diphenylsiloxyphenyltrimethicone,
diphenylsiloxyphenyldimethicone,
trimethylpentaphenyl trisiloxane,
phenyl dimethicones,
phenyltrimethylsiloxydiphenylsiloxanes,
diphenyl dimethicones,
diphenylmethyldiphenyltrisiloxanes and
2-phenylethyl trimethylsiloxysilicates, and
mixtures thereof.

Preferably, the weight-average molecular weight of the non-volatile phenyl silicone oil according to the invention ranges from 500 to 10 000 g/mol.

Non Volatile Phenylated Silicone Oil Having at Least a Dimethicone Part

According to a first embodiment, the non volatile phenylated silicone oil is chosen from phenyl dimethicone oil(s), (which means a phenyl silicone oil having at least a dimethicone part). Preferably, non volatile silicone oil is chosen from oils corresponding to formula (VII)

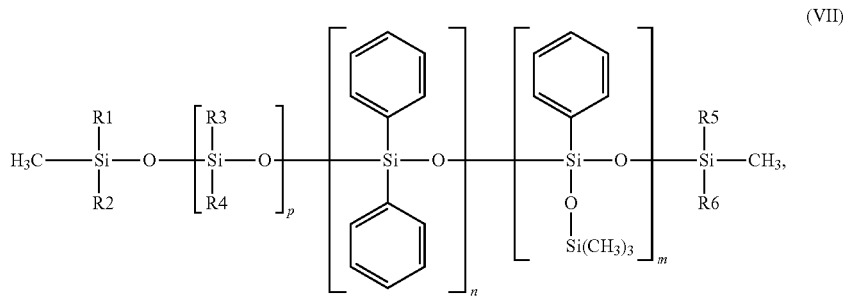

wherein $R_1$ to $R_6$, m, n and p, are as defined before.

A) According to a first embodiment, m=0 and n and p are independently of each other, integers between 1 and 100, in formula (VII). Preferably R1 to R6 are methyl radicals. According to this embodiment, the silicone oil is preferably chosen from diphenyl dimethicone such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt).

B) According to a second embodiment, p is between 1 and 100 in formula (VII), the sum n+m is between 1 and 100, and n=0, in formula (VII). As silicone oils of formula (VII) wherein n=0 and $R_1$ to $R_6$ are methyl radicals, it is especially possible to use a silicone oil chosen from trimethylsiloxyphenyldimethicone such as Belsil PDM 1000 from Wacker.

According to a first embodiment, the silicon oil is a phenyl silicone oil having at least a dimethicone part, and is preferably chosen from:

diphenyl dimethicone such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt);
trimethyl siloxyphenyl dimethicone, such as Belsil PDM 1000 from Wacker, trimethylsiloxyphenyltrimethicone, trimethyl pentaphenyl trisiloxane such as PH-1555 HRI or Dow Corning 555 Cosmetic Fluid from Dow Corning, and
mixture thereof.

According to a preferred embodiment, the composition according to the invention is free of non volatile phenylated silicone oil(s) having at least a dimethicone part.

This embodiment exhibit particular advantages regarding the homogeneity and the stability of the composition, as well as of the deposit on the skin and/or the lips.

According to a preferred embodiment, the composition according to the invention is free of non volatile silicone oil(s) having at least a dimethicone part.

Non Volatile Phenyl Silicone Oil Having No Dimethicone Part

According to a second preferred embodiment, the silicone oil is a phenyl silicone oil having no dimethicone part, or mixture thereof.

Preferably, the non volatile phenylated silicone oil having no dimethicone part is chosen from:

a) the phenyl silicone oils corresponding to the following formula (I):

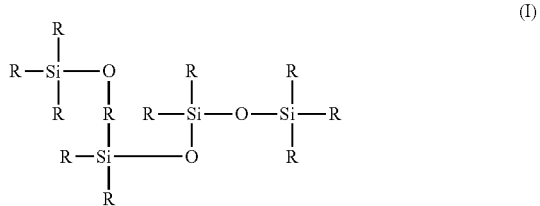

in which the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

b) the phenyl silicone oils corresponding to the following formula (II):

$$R-\underset{\underset{R}{|}}{\overset{\overset{R}{|}}{Si}}-O-\underset{\underset{R}{|}}{\overset{\overset{R}{|}}{Si}}-O-\underset{\underset{R}{|}}{\overset{\overset{R}{|}}{Si}}-R \quad (II)$$

in which the groups R represent, independently of each other, a methyl or a phenyl, with the proviso that at least one group R represents a phenyl. Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes.

c) the phenyl silicone oils corresponding to the following formula (III):

$$Me-\underset{\underset{PH_2}{\backslash}}{\overset{\overset{Ph}{/}}{Si}}-O-\underset{\underset{Me}{\backslash}}{\overset{\overset{Ph}{/}}{Si}}-O-\underset{\underset{Ph}{\backslash}}{\overset{\overset{Ph}{/}}{Si}}-Me \quad (III)$$

in which Me represents methyl, Ph represents phenyl. Such a phenyl silicone is especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane), or Tetramethyl Tetraphenyl Trisiloxane sold under the reference Dow Corning 554 Cosmetic Fluid by Dow Corning may also be used.

e) the phenyl silicone oils corresponding to formula (V') below:

$$Me-\underset{\underset{Me}{|}}{\overset{\overset{Me}{|}}{Si}}-\left[O-\underset{\underset{Me}{|}}{\overset{\overset{Me}{|}}{Si}}\right]_y-\left[O-\underset{\underset{Ph}{|}}{\overset{\overset{OR'}{|}}{Si}}\right]_z-O-Si(CH_3)_3 \quad (V')$$

in which Me is methyl and Ph is phenyl, OR' represents a group —OSiMe$_3$ and y is 0 and z ranges between 1 and 1000, in particular, z is such that compound (V') is a non-volatile oil.

According to a second embodiment, y is equal to 0. Use may be made, for example, of phenyl trimethylsiloxy trisiloxane, sold especially under the reference Dow Corning 556 Cosmetic Grade Fluid (DC556), g) the phenyl silicone oils corresponding to formula (VIII) below, and mixtures thereof:

$$CH_3-\underset{\underset{R}{|}}{\overset{\overset{R}{|}}{Si}}-O-\left[\underset{|}{\overset{|}{Si}}-O\right]_n-\left[\underset{\underset{CH_3-\underset{\underset{CH_3}{|}}{\overset{\overset{CH_3}{|}}{Si}}-CH_3}{|}}{\overset{|}{Si}}-O\right]_m-\underset{\underset{R}{|}}{\overset{\overset{R}{|}}{Si}}-CH_3 \quad (VIII)$$

in which:
R, independently of each other, are saturated or unsaturated, linear, cyclic or branched $C_1$-$C_{30}$ hydrocarbon-based radicals, preferably R is a $C_1$-$C_{30}$ alkyl radical, an aryl radical or an aralkyl radical,
m and n are, independently of each other, integers between 0 and 100, with the proviso that the sum n+m is between 1 and 100.

Preferably, R, independently of each other, represent a saturated or unsaturated linear or branched $C_1$-$C_{30}$, hydrocarbon radical, preferably saturated, and especially $C_1$-$C_{12}$ hydrocarbon-based radical, in particular $C_3$-$C_{16}$ and more particularly $C_4$-$C_{10}$, or a monocyclic or polycyclic $C_6$-$C_{14}$ and especially $C_{10}$-$C_{13}$ aryl radical, or an aralkyl radical. Preferably, R may each represent a methyl, ethyl, propyl, butyl, isopropyl, decyl, dodecyl or octadecyl radical, or alternatively a phenyl, tolyl, benzyl or phenethyl radical. R may especially be identical, and in addition may be a methyl radical. Preferably, m=1 or 2 or 3, and/or n=0 and/or p=0 or 1 may apply, in formula (VII').

According to a preferred embodiment, n is an integer between 0 and 100 and m is an integer between 1 and 100, with the proviso that the sum n+m is between 1 and 100, in formula (VIII). Preferably R is methyl radical.

According to one embodiment, a phenyl silicone oil of formula (VIII) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt) may be used.

According to this embodiment, the non volatile phenyl silicone oil is preferably chosen from phenyl trimethicones; such as DC556 from Dow Corning (22.5 cSt), the oil diphenylsiloxy phenyltrimethicone such as KF56 A from Shin Etsu, the oil Silbione 70663 V30 from Rhone-Poulenc (28 cSt). The values in parentheses represent the viscosities at 25° C.

According to this embodiment, when n=0, said silicone oil is preferably DC556 from Dow Corning, and when m and n are between 1 and 100, said said silicone oil is preferably KF56 A from Shin Etsu.

Preferably the non volatile phenylated silicone oil having no dimethicone part may be chosen from:
phenyl trimethylsiloxy trisiloxane, phenyl trimethicones; such as DC556 from Dow Corning,
Tetramethyl Tetraphenyl Trisiloxane, such as PH-1554 HRI or Dow Corning 554 Cosmetic Fluid from Dow Corning
diphenylsiloxy phenyltrimethicone such as KF56 A from Shin Etsu, the oil Silbione 70663V30 from Rhône-Poulenc,
trimethyl pentaphenyl trisiloxane such as PH-1555 HRI or Dow Corning 555 Cosmetic Fluid from Dow Corning, and
mixture thereof.

It should be noted that, among the abovementioned silicone oils, the phenyl silicone oils having no dimethicone part prove to be particularly advantageous. They can especially impart a good level of gloss to the deposit on the skin or the lips made with the composition according to the invention, without generating any tack, and enable forming a non transfer deposit in association with the non volatile hydrocarbonated oil.

Preferably, the composition according to the invention comprises a mixture of at least two different non volatile phenyl silicone oils having no dimethicone part, preferably from trimethyl pentaphenyl trisiloxane and diphenylsiloxy phenyltrimethicone.

2. Non-Phenylated Non Volatile Silicone Oil

The composition according to the invention may also comprise a non volatile non phenylated silicone oil as non volatile silicone oil.

The expression "non phenylated silicone oil" or "non phenyl silicone oil" are equivalent and both means a silicon oil having no phenyl substituent.

Representative examples of these non-volatile non phenylated silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

According to a first embodiment, the non volatile silicon oil is a non phenylated oil, preferably chosen from polydimethylsiloxanes; alkyl dimethicones; vinyl methyl methicones; and also silicones modified with optionally fluorinated aliphatic groups, or with functional groups such as hydroxyl, thiol and/or amine groups.

The non volatile non phenylated silicon oil is preferably chosen from dimethicone oils, preferably chosen from polydimethylsiloxanes; alkyl dimethicones.

"Dimethicone" (INCI Name) corresponds to polydimethylsiloxane (chemical name).

Non-phenylated non-volatile silicone oils can be chosen from:
- non-volatile polydimethylsiloxanes (PDMS),
- PDMSs comprising alkyl or alkoxy groups, which are pendent and/or at the end of the silicone chain, these groups each containing from 2 to 24 carbon atoms, such as cetyldimethicone sold under the commercial reference ABIL WAX 9801 from Evonik Goldschmidt,
- PDMSs comprising aliphatic and/or aromatic groups, or functional groups such as hydroxyl, thiol and/or amine groups,
- polyalkylmethylsiloxanes such as cetyldimethicone sold under the commercial reference ABIL WAX 9801 from Evonik Goldschmidt, or polyalkylmethylsiloxane optionally substituted with a fluorinated group, such as polymethyltrifluoropropyldimethylsiloxanes,
- polyalkylmethylsiloxanes substituted with functional groups such as hydroxyl, thiol and/or amine groups,
- polysiloxanes modified with fatty acids, fatty alcohols or polyoxyalkylenes, and mixtures thereof.

According to one embodiment, a composition according to the invention contains at least one non-phenylated linear silicone oil.

These non-volatile non phenylated linear silicone oils may be chosen from polydimethylsiloxanes; alkyl dimethicones; vinyl methyl methicones; and also silicones modified with optionally fluorinated aliphatic groups, or with functional groups such as hydroxyl, thiol and/or amine groups.

The non-phenylated linear silicone oil may be chosen especially from the silicones of formula (I):

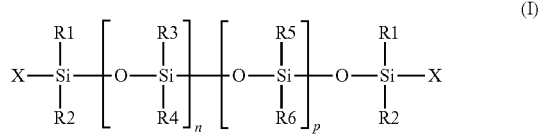

in which:
$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular whose viscosity at 25° C. is between 9 centistokes (cSt) ($9 \times 10^{-6}$ m$^2$/s) and 800 000 cSt.

As non-volatile non phenylated silicone oils that may be used according to the invention, mention may be made of those for which:
- the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
- the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker,
- the substituents $R_1$ to $R_6$ and X represent a methyl group, and p and n are such that the viscosity is 350 cSt, such as the product sold under the name Dow Corning 200 Fluid 350 CS by the company Dow Corning,
- the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to a particular embodiment, the composition comprises a polyalkylmethylsiloxanes, such as cetyldimethicone sold under the commercial reference ABIL WAX 9801 from Evonik Goldschmidt. Preferably, the composition comprises from 0.1 to 10% polyalkylmethylsiloxanes, such as cetyldimethicone.

In particular, a composition according to the invention, preferably for caring for and/or making up the lips and more particularly of lipstick type may comprise from 0.1% to 70% by total weight of non volatile non phenylated silicone oil(s), preferably from 0.1 to 50%, preferably from 1 to 30%, relative to the total weight of the composition.

Preferably, the composition according to the invention comprises from 45% to 70% by total weight of total content of non volatile silicone oil(s), preferably between 45 and 60% by weight, or mixture thereof relative to the total weight of the composition.

According to a particular embodiment, the composition according to the invention may comprise no non volatile non phenylated silicone oil. According to this particular embodiment, all the non volatile silicon oil(s) are phenylated.

Preferably, when the composition comprises at least a non volatile non phenylated silicone oil, the weight ratio of the total non volatile phenylated silicone oil(s) to the total non volatile non phenylated dimethicone oil(s) is superior or equal to 1, preferably comprised between 1 and 100, more preferably comprised between 1 and 50.

Preferably, when the composition comprises at least a non volatile non phenylated silicone oil, the weight ratio of the total non volatile phenylated silicone oil(s) to the total non volatile non phenylated dimethicone oil(s) is comprised between 1 and 30, more preferably comprised between 2 and 10.

Non Volatile Hydrocarbonated Apolar Oil:

The composition according to the invention comprises at least one non volatile apolar hydrocarbonated oil (also called apolar "hydrocarbon-based" oil).

More particularly, the composition according to the invention comprises from 5% to 30% by total weight of non volatile hydrocarbonated apolar oil(s), relative to the total weight of the composition. Preferably, the composition according to the invention comprises from 5% to 25% by total weight of non volatile hydrocarbonated apolar oil(s), preferably from 8% to 25% by weight, relative to the total weight of the composition.

For the purposes of the present invention, the term "apolar oil" means an oil whose solubility parameter at 25° C., $\delta_a$, is equal to 0 $(J/cm^3)^{1/2}$.

The definition and calculation of the solubility parameters in the Hansen three-dimensional solubility space are described in the article by C. M. Hansen: "The three dimensional solubility parameters", J. Paint Technol. 39, 105 (1967).

According to this Hansen space:

$\delta_D$ characterizes the London dispersion forces derived from the formation of dipoles induced during molecular impacts;

$\delta_P$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

The term "hydrocarbon-based oil" (or "hydrocarbonated oil", or "hydrocarbon oil") means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

These oils may be of plant, mineral or synthetic origin.

Preferably, the non-volatile apolar hydrocarbon-based oil may be chosen from linear or branched hydrocarbons of mineral or synthetic origin.

In particular said-volatile apolar hydrocarbon-based oil may be chosen from:

liquid paraffin or derivatives thereof,
squalane,
isoeicosane,
naphthalene oil,
polybutylenes such as Indopol H-100 (molar mass or MW=965 g/mol), Indopol H-300 (MW=1340 g/mol) and Indopol H-1500 (MW=2160 g/mol) sold or manufactured by the company Amoco,
polyisobutenes,
hydrogenated polyisobutylenes such as Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), or alternatively Parleam Lite sold by NOF Corporation,
decene/butene copolymers, polybutene/polyisobutene copolymers, especially Indopol L-14, polydecenes and hydrogenated polydecenes such as: Puresyn 10 (MW=723 g/mol) and Puresyn 150 (MW=9200 g/mol) sold or manufactured by the company Mobil Chemicals, or alternatively Puresyn 6 sold by ExxonMobil Chemical), and
mixtures thereof.

Preferably, the composition according to the invention comprises at least one non volatile hydrocarbon-based apolar oil, preferably chosen from polybutenes, polyisobutenes, hydrogenated polyisobutenes, polydecenes and/or hydrogenated polydecenes, and mixtures thereof.

Preferably said non volatile apolar hydrocarbonated oil comprises at least a hydrogenated polydecene and/or hydrogenated polyisobutene, or mixture thereof. Preferably said non volatile hydrocarbon oil comprise at least a hydrogenated polydecene and/or hydrogenated polyisobutene, preferably in a total content ranging from 5 to 30%, preferably from 10 to 30% by weight, relative to the total weight of the composition.

Preferably said non volatile hydrocarbon oil comprise at least hydrogenated polydecene and/or hydrogenated polyisobutene, preferably in a total content ranging from 10 to 25%, by weight, relative to the total weight of the composition.

Preferably, the weight ratio of the total apolar non volatile hydrocarbonated oil(s) to the total non volatile silicone oil(s) comprised between 0.1 and 10, more preferably comprised between 0.1 and 5, and preferably comprised between 0.1 and 1.

Preferably, the weight ratio of the total non volatile apolar hydrocarbonated oil(s) to the total non volatile silicone oil(s) is comprised between 0.1 and 0.5.

Preferably, the weight ratio of the total apolar non volatile hydrocarbonated oil(s) to the total non volatile phenyl silicone oil(s) is between 0.1 and 10, more preferably comprised between 0.1 and 5, and preferably comprised between 0.1 and 1, more preferably between 0.1 and 0.5.

Preferably, when the composition comprises at least a non volatile non phenylated dimethicone, the weight ratio of the total apolar non volatile hydrocarbonated oil(s) to the total non volatile non phenylated dimethicone oil(s) is between 0.1 and 20, preferably between 0.1 and 10.

The composition according to the invention may also comprises at least one additional compound, preferably chosen from a hydrocarbonated polar oil, and/or an additional volatile oil, and/or a fatty pasty compound, and/or a filler and/or a colouring agent, and/or mixture thereof.

Non Volatile Hydrocarbonated Polar Oil

According to a preferred embodiment, the composition according to the invention may comprise an additional non volatile polar hydrocarbonated oil.

For the purposes of the present invention, the term "polar oil" means an oil whose solubility parameter at 25° C., $\delta_a$, is other than 0 $(J/cm^3)^{1/2}$.

These oils may be of plant, mineral or synthetic origin.

In particular, the additional hydrocarbon-based non-volatile polar oil may be chosen from the list of oils below, and mixtures thereof:

hydrocarbon-based plant oils such as liquid triglycerides of fatty acids containing from 4 to 10 carbon atoms, for instance heptanoic or octanoic acid triglycerides or jojoba oil;

ester oils, preferably chosen from:
fatty acid esters, in particular of 4 to 22 carbon atoms, and especially of octanoic acid, heptanoic acid, lanolic acid, oleic acid, lauric acid or stearic acid, for instance propylene glycol dioctanoate, propylene glycol monoisostearate or neopentyl glycol diheptanoate;

synthetic esters, for instance the oils of formula $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms, on condition that $R_1+R_2 \geq 16$, for instance purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, oleyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate; preferably, the preferred synthetic esters $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms are such that $R_1$ and $R_2 \geq 20$;

inear fatty acid esters with a total carbon number ranging from 35 to 70, for instance pentaerythrityl tetrapelargonate (MW=697 g/mol);

hydroxylated esters, preferably with a total carbon number ranging from 35 to 70, for instance polyglyceryl-2 triisostearate (MW=965 g/mol), isostearyl lactate, octyl hydroxystearate, octyldodecyl hydroxystearate, diisostearyl malate, glyceryl stearate; diethylene glycol diisononanoate;

esters of aromatic acids and of alcohols comprising 4 to 22 atoms, such as tridecyl trimellitate (MW=757 g/mol);

$C_{24}$-$C_{28}$ esters of branched fatty alcohols or fatty acids such as those described in patent application EP-A-0 955 039, and especially triisoarachidyl citrate (MW=1033.76 g/mol), pentaerythrityl tetraisononanoate (MW=697 g/mol), glyceryl triisostearate (MM=891 g/mol), glyceryl tris(2-decyl)tetradecanoate (MW=1143 g/mol), pentaerythrityl tetraisostearate (MW=1202 g/mol), polyglyceryl-2 tetraisostearate (MW=1232 g/mol) or pentaerythrityl tetrakis(2-decyl)tetradecanoate (MW=1538 g/mol), polyesters resulting from the esterification of at least one hydroxylated carboxylic acid triglyceride with an aliphatic monocarboxylic acid and with an aliphatic dicarboxylic acid, which is optionally unsaturated, for instance the succinic acid and isostearic acid castor oil sold under the reference Zenigloss by Zenitech;

esters of a diol dimer and of a diacid dimer of general formula HO—$R^1$—(—OCO—$R^2$—COO—$R^1$—)$_h$—OH, in which:

$R^1$ represents a diol dimer residue obtained by hydrogenation of dilinoleic diacid, $R^2$ represents a hydrogenated dilinoleic diacid residue, and h represents an integer ranging from 1 to 9, especially the esters of dilinoleic diacids and of dilinoleyl diol dimers sold by the company Nippon Fine Chemical under the trade names Lusplan DD-DA5® and DD-DA7®, polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or copolymers of polyols and of diacid dimers, and esters thereof, such as Hailuscent ISDA;

fatty alcohols containing from 12 to 26 carbon atoms, which are preferably branched, for instance octyldodecanol, 2-butyloctanol, 2-hexyldecanol, 2-undecylpentadecanol and oleyl alcohol;

$C_{12}$-$C_{22}$ higher fatty acids, such as oleic acid, linoleic acid and linolenic acid, and mixtures thereof;

oils of plant origin, such as sesame oil (820.6 g/mol);

fatty acids containing from 12 to 26 carbon atoms, for instance oleic acid;

dialkyl carbonates, the two alkyl chains possibly being identical or different, such as dicaprylyl carbonate sold under the name Cetiol CC® by Cognis; and vinylpyrrolidone copolymers such as the vinylpyrrolidone/1-hexadecene copolymer, Antaron V-216 sold or manufactured by the company ISP (MW=7300 g/mol).

Preferably, the composition according to the invention comprises at least one additional non-volatile polar hydrocarbon oil chosen from:

vinylpyrrolidone copolymers, preferably such as the vinylpyrrolidone/1-hexadecene copolymer;

hydroxylated esters, preferably with a total carbon number ranging from 35 to 70, preferably chosen from polyglyceryl-2 triisostearate, isostearyl lactate, octyl hydroxystearate, octyldodecyl hydroxystearate, diisostearyl malate, glyceryl stearate; diethylene glycol diisononanoate;

oils from plant origin preferably chosen from liquid triglycerides of fatty acids;

$C_{24}$-$C_{28}$ esters of branched fatty alcohols or fatty acids preferably chosen from triisoarachidyl citrate (MW=1033.76 g/mol), pentaerythrityl tetraisononanoate (MW=697 g/mol), glyceryl triisostearate (MM=891 g/mol), glyceryl tris(2-decyl)tetradecanoate (MW=1143 g/mol), pentaerythrityl tetraisostearate (MW=1202 g/mol), polyglyceryl-2 tetraisostearate (MW=1232 g/mol) or pentaerythrityl tetrakis(2-decyl) tetradecanoate (MW=1538 g/mol).

synthetic esters of formula $R_1COOR_2$ in which $R_1$ represents a linear or branched fatty acid residue containing from 4 to 40 carbon atoms and $R_2$ represents a hydrocarbon-based chain that is especially branched, containing from 4 to 40 carbon atoms, provided that $R_1+R_2 \geq 16$; and mixtures thereof.

A composition according to the invention may comprise a content of additional non volatile polar hydrocarbonated oil ranging from 0.1% to 50%, for example from 0.1% to 40% by weight and preferably from 0.5% to 30% by weight, relative to the total weight of the composition.

A composition according to the invention may comprise a content of additional non volatile polar hydrocarbonated oil ranging from 1% to 20% by weight, preferably from 1 to 10% by weight, relative to the total weight of the composition.

According to a preferred embodiment, the composition according to the invention comprises a content of non volatile polar hydrocarbonated oil comprised between 0.1 and 10%. According to another embodiment, the composition according to the invention is free from non volatile polar hydrocarbonated oil.

Preferably, the weight ratio of the total non volatile hydrocarbonated oil(s) (ie apolar and polar if present) to the total non volatile silicone oil(s) is comprised between 0.1 and 10, more preferably comprised between 0.1 and 5, and preferably comprised between 0.1 and 1.

Preferably, the weight ratio of the total non volatile hydrocarbonated oil(s) (ie apolar and polar if present) to the total non volatile silicone oil(s) is comprised between 0.1 and 0.5.

A cosmetic makeup and/or care composition according to the invention also comprises a cosmetically acceptable medium that may comprise the usual ingredients, as a function of the intended use of the composition.

Additional Fatty Phase

According to one embodiment, the composition according to the invention may comprise, besides said non volatile silicone oil and said non volatile hydrocarbonated oil, an additional liquid fatty phase, preferably chosen from non volatile polar hydrocarbonated oils described before, and/or volatile silicone oils.

The additional liquid fatty phase may represent from 0.1% to 80% by weight relative to the total weight of the composition.

In particular, a composition according to the invention and/or used in a composition according to the invention may comprise from 0.1% to 75% by weight of an additional liquid fatty phase relative to its total weight.

More particularly, a composition according to the invention and/or used in a composition according to the invention may comprise from 0.5% to 70% by weight of an additional liquid fatty phase relative to its total weight.

Volatile Oil

According to one embodiment, the composition according to the invention may comprise a volatile oil.

Thus, a composition under consideration according to the invention may advantageously comprise one or more oils, which may be chosen especially from volatile hydrocarbon-based oils, volatile silicone oil and fluoro oils, and mixtures thereof.

For the purposes of the invention, the term "volatile oil" means an oil that is capable of evaporating on contact with keratin materials in less than one hour, at room temperature (25° C.) and atmospheric pressure (760 mmHg). The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.1 to 10 mmHg).

The oils may be of animal, plant, mineral or synthetic origin.

Volatile Fluoro Oil

The term "fluoro oil" means an oil comprising at least one fluorine atom.

The fluoro oils that may be used in the invention may be chosen from fluorosilicone oils, fluoro polyethers and fluorosilicones as described in document EP-A-847 752, and perfluoro compounds.

According to the invention, the term "perfluoro compounds" means compounds in which all the hydrogen atoms have been replaced with fluorine atoms.

According to one preferred embodiment, the fluoro oil according to the invention is chosen from perfluoro oils. As examples of perfluoro oils that may be used in the invention, mention may be made of perfluorodecalins and perfluoroperhydrophenanthrenes.

According to one preferred embodiment, the fluoro oil is chosen from perfluoroperhydrophenanthrenes, and especially the Fiflow® products sold by the company Creations Couleurs. In particular, use may be made of the fluoro oil whose INCI name is perfluoroperhydrophenanthrene, sold under the reference Fiflow 220 by the company F2 Chemicals.

Volatile Hydrocarbon Oil

According to a preferred embodiment, the composition according to the invention further comprises a volatile hydrocarbonated oil such as isododecane and/or isohexadecane.

Such compound is compatible with the non volatile hydrocarbonated and silicone oil and improves the spreadability during application and the transfer resistance of the deposit.

The term "hydrocarbon-based oil" (or "hydrocarbonated oil", or "hydrocarbon oil") means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The volatile hydrocarbon-based oils may be chosen from hydrocarbon-based oils containing from 8 to 16 carbon atoms, and especially $C_8$-$C_{16}$ branched alkanes (also known as isoparaffins), for instance isododecane (also called 2,2,4,4,6-pentamethylheptane), isodecane and isohexadecane, and mixture thereof.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

The term "hydrocarbon-based oil" is intended to mean an oil formed essentially, or even constituted, of carbon and hydrogen atoms, and optionally of oxygen and nitrogen atoms, and containing no silicon or fluorine atoms. It may contain alcohol, ester, ether, carboxylic acid, amine and/or amide groups.

According to one embodiment, a composition according to the invention also comprises at least isododecane and/or isohexadecane.

According to one embodiment, the composition is free of additional volatile hydrocarbonated oil other than isododecane and/or isohexadecane.

More particularly, the composition according to the invention contains between 0.1% and 20% by weight of volatile oil, preferably isododecane and/or isohexadecane, relative to its total weight.

Preferably, the composition according to the invention contains between 1% and 15% by weight of volatile oil, preferably of isododecane and/or isohexadecane, relative to its total weight.

Advantageously, the composition according to the invention contains between 1% and 10% by weight of volatile oil, preferably of isododecane and/or isohexadecane, relative to its total weight.

As other volatile hydrocarbon-based solvents (oils) that can be used in the composition according to the invention, mention may also be made of ketones which are liquid at ambient temperature, such as methyl ethyl ketone or acetone; short-chain esters (containing from 3 to 8 carbon atoms in total), such as ethyl acetate, methyl acetate, propyl acetate or n-butyl acetate; ethers which are liquid at ambient temperature, such as diethyl ether, dimethyl ether or dichlorodiethyl ether; alcohols, and in particular linear or branched lower monoalcohols containing from 2 to 5 carbon atoms, for instance ethanol, isopropanol or n-propanol.

According to one preferred embodiment, the volatile oil has a flash point of greater than 65° C., and better still greater than 80° C. By way of example of such a volatile oil, mention may be made of isohexadecane.

Advantageously, the composition according to the invention comprises less than 5% and better still less than 2% by weight of volatile oil having a flash point of less than 80° C., relative to the total weight of the composition. Preferably, the composition according to the invention is free of volatile oil having a flash point of less than 80° C.

Volatile Silicone Oils

According to an embodiment, the compositions according to the invention may comprise at least one volatile silicone oil.

The term "silicone oil" is intended to mean an oil comprising at least one silicon atom, and in particular comprising Si—O groups.

The volatile silicone oil that may be used in the invention may be chosen from silicone oils especially having a viscosity ≤8 centistokes (cSt) ($8 \times 10^{-6}$ m$^2$/s) and preferably greater than 0.5 cSt.

The term "silicone oil" is intended to mean an oil comprising at least one silicon atom, and in particular comprising Si—O groups.

The volatile silicone oil that can be used in the invention may be chosen from silicone oils having a flash point ranging from 40° C. to 150° C., preferably having a flash point of greater than 55° C. and less than or equal to 105° C., and preferentially ranging from 65° C. to 95° C. The flash point is in particular measured according to ISO standard 3679.

The volatile silicone oil may be chosen from linear or cyclic silicone oils such as linear or cyclic polydimethylsiloxanes (PDMSs) having from 3 to 7 silicon atoms.

Volatile silicone oils that may more particularly be mentioned include decamethylcyclopentasiloxane sold especially under the name DC-245 by the company Dow Corning, dodecamethylcyclohexasiloxane sold especially under the name DC-246 by the company Dow Corning, octamethyltrisiloxane sold especially under the name DC-200 Fluid 1 cSt by the company Dow Corning, polydimethylsiloxanes such as decamethyltetrasiloxane sold especially under the name DC-200 Fluid 1.5 cSt by the company Dow Corning and DC-200 Fluid 5 cSt sold by the company Dow Corning, octamethylcyclotetrasiloxane, heptamethylhexyltrisiloxane, heptamethylethyltrisiloxane, heptamethyloctyltrisiloxane and dodecamethylpentasiloxane, octyl trimethicone, hexyl trimethicone, decamethylcyclopentasiloxane (cyclopentasiloxane or D5), octamethylcyclotetrasiloxane (cyclotetradimethylsiloxane or D4), dodecamethylcyclohexasiloxane (D6), decamethyltetrasiloxane (L4), KF 96 A from Shin Etsu, and mixtures thereof.

Solid Fatty Substances

The composition according to the invention comprises at least one solid fatty substance especially at least a wax.

Waxes

The composition according to the invention comprises from 3 to 30% of wax(es). The composition according to the invention may comprise a wax or a mixture of different waxes.

The term "wax" for the purposes of the present invention, meas a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for the invention may have a melting point of greater than or equal to 45° C. and in particular greater than or equal to 55° C.

By bringing the wax to the liquid state (melting), it is possible to make it miscible with the oils that may be present and to form a microscopically uniform mixture, but on returning the temperature of the mixture to room temperature, recrystallization of the wax in the oils of the mixture is observed.

For the purposes of the invention, the melting point corresponds to the temperature of the most endothermic peak observed by thermal analysis (DSC) as described in standard ISO 11357-3; 1999. The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

The wax may especially have a hardness ranging from 0.05 MPa to 15 MPa and preferably ranging from 6 MPa to 15 MPa. The hardness is determined by measuring the compression force, measured at 20° C., using a texturometer sold under the name TA-TX2i by the company Rheo, equipped with a stainless-steel cylinder 2 mm in diameter, moving at a measuring speed of 0.1 mm/s, and penetrating into the wax to a penetration depth of 0.3 mm.

Apolar Waxes

According to a preferred embodiment, the composition according to the invention comprises at least an apolar wax, preferably a hydrocarbon based wax.

For the purposes of the present invention, the term "apolar wax" means a wax whose solubility parameter at 25° C. as defined before, $\delta_a$, is equal to 0 (J/cm$^3$)$^{1/2}$.

The definition and calculation of the solubility parameters in the Hansen three-dimensional solubility space are described in the article by C. M. Hansen: "The three dimensional solubility parameters" J. Paint Technol. 39, 105 (1967).

According to this Hansen space:
  $\delta_D$ characterizes the London dispersion forces derived from the formation of dipoles induced during molecular impacts;
  $\delta_p$ characterizes the Debye interaction forces between permanent dipoles and also the Keesom interaction forces between induced dipoles and permanent dipoles;
  $\delta_h$ characterizes the specific interaction forces (such as hydrogen bonding, acid/base, donor/acceptor, etc.); and
  $\delta_a$ is determined by the equation: $\delta_a = (\delta_p^2 + \delta_h^2)^{1/2}$.

The parameters $\delta_p$, and $\delta_D$ and $\delta_a$ are expressed in (J/cm$^3$)$^{1/2}$.

Apolar waxes are in particular hydrocarbon-based waxes. Such waxes are particularly formed solely from carbon and hydrogen atoms, and free of heteroatoms such as N, O and P.

In particular, the term "apolar wax" means a wax that is formed exclusively from apolar wax and not from a mixture also comprising other types of waxes that are not apolar waxes.

As illustrations of apolar waxes that are suitable for use in the invention, mention may be made especially of hydrocarbon-based waxes, for instance microcrystalline waxes, paraffin waxes, ozokerite and polyethylene waxes.

Polyethylene waxes that may be mentioned include Performalene 500-L Polyethylene and Performalene 400 Polyethylene sold by New Phase Technologies.

An ozokerite that may be mentioned is Ozokerite Wax SP 1020 P.

As microcrystalline waxes that may be used, mention may be made of Multiwax W 445® sold by the company Sonneborn and Microwax HW® and Base Wax 30540® sold by the company Paramelt.

As microwaxes that may be used in the compositions according to the invention as apolar wax, mention may be made especially of polyethylene microwaxes such as those sold under the names Micropoly 200®, 220®, 220L® and 250S® by the company Micro Powders.

Preferably, the composition may contain from 3% to 30%, better still from 3% to 20% by weight or even between 3% and 15% by total weight of apolar waxes, relative to the total weight of the composition.

Preferably, the composition may contain from 3% to 30%, better still from 4% to 15% by total weight of apolar waxes, relative to the total weight of the composition.

Preferably, the apolar wax is chosen from microcrystalline waxes, paraffin waxes, ozokerite and polyethylene waxes, and/or mixture thereof.

Polar Waxes

The composition according to the invention may also comprise, besides the apolar wax, an additional wax, for instance an polar wax.

For the purposes of the present invention, the term "polar wax" means a wax whose solubility parameter at 25° C., $\delta_a$, is other than 0 $(J/cm^3)^{1/2}$.

In particular, the term "polar wax" means a wax whose chemical structure is formed essentially from, or even constituted by, carbon and hydrogen atoms, and comprising at least one highly electronegative heteroatom such as an oxygen, nitrogen or phosphorus atom.

The waxes may especially be hydrocarbon-based or silicone waxes.

The term "hydrocarbon-based wax" means a wax formed essentially from, or even constituted by, carbon and hydrogen atoms, and possibly oxygen and nitrogen atoms, and not containing any silicon or fluorine atoms. It may contain alcohol, ester, ether, carboxylic acid, amine and/or amide groups.

The term "silicone wax" means an oil comprising at least one silicon atom, and especially comprising Si—O groups.

Preferably, the polar wax is hydrocarbon based. As illustrations of hydrocarbon-based waxes that are suitable for the invention, mention may be made of beeswax, lanolin wax, rice bran wax, carnauba wax, candelilla wax, shellac wax; montan wax, orange wax and lemon wax, laurel wax and olive wax. According to one preferred embodiment, the polar wax is an ester wax. The term "ester wax" means according to the invention a wax comprising at least one ester function.

The following may especially be used as ester wax:
ester waxes such as:
i) the waxes of formula $R_1COOR_2$ in which $R_1$ and $R_2$ represent linear, branched or cyclic aliphatic chains in which the number of atoms ranges from 10 to 50, which may contain a heteroatom such as O, N or P, and whose melting point ranges from 25 to 120° C.

In particular, a $C_{20}$-$C_{40}$ alkyl(hydroxystearyloxy)stearate (the alkyl group containing from 20 to 40 carbon atoms), alone or as a mixture, or a $C_{20}$-$C_{40}$-alkyl stearate, may be used as ester wax. Such waxes are especially sold under the names Kester Wax K 82 P®, Hydroxypolyester K 82 P®, Kester Wax K 80 P® or Kester Wax K82H by the company Koster Keunen.

It is also possible to use an ester of polyethylene glycol and of montanic acid (octacosanoic acid), such as the wax Licowax KPS Flakes (INCI name: glycol montanate) sold by the company Clariant.

ii) bis(1,1,1-trimethylolpropane)tetrastearate, sold under the name Hest 2T-4S® by the company Heterene, iii) waxes of diesters of a dicarboxylic acid of general formula $R^3$—(—OCO—$R^4$—COO—$R^5$), in which $R^3$ and $R^5$ are identical or different, preferably identical, and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms), which may or may not contain one or more unsaturations, and is preferably linear and unsaturated, iv) waxes obtained by hydrogenation of castor oil esterified with cetyl alcohol, sold under the names Phytowax ricin 16L64® and 22L73 ® by the company Sophim. Such waxes are described in patent application FR-A-2 792 190.

According to another embodiment, the polar wax may be an alcohol wax. According to the invention, the term "alcohol wax" means a wax comprising at least one alcohol function, i.e. comprising at least one free hydroxyl (OH) group.

An example of an alcohol wax that may be mentioned is the wax Performacol 550-L Alcohol from New Phase Technologies.

According to a preferred embodiment, the composition according to the invention is free of polar waxes.

Pasty Fatty Substances

According to a first embodiment, the composition is free of pasty fatty substances.

According to a second preferred embodiment, the composition comprises at least one pasty fatty substance. According to this embodiment, preferably, the amount of pasty fatty substance in the makeup and/or care composition according to the invention is between 0.5% and 60% by weight, especially from 1% to 50% by weight or even 2% to 40% by weight, relative to the total weight of the composition.

The term "pasty", within the meaning of the present invention, is understood to mean a lipophilic fatty compound with a reversible solid/liquid change of state exhibiting, in the solid state, an anisotropic crystalline arrangement and comprising, at a temperature of 23° C., a liquid fraction and a solid fraction.

The term "pasty compound", within the meaning of the invention, is understood to mean a compound having a hardness at 20° C. ranging from 0.001 to 0.5 MPa, preferably from 0.002 to 0.4 MPa.

The hardness is measured according to a method of penetration of a probe into a sample of compound and in particular using a texture analyser (for example, the TA-XT2i from Rheo) equipped with a stainless steel cylinder with a diameter of 2 mm. The hardness measurement is carried out at 20° C. at the centre of 5 samples. The cylinder is introduced into each sample at a pre-rate of 1 mm/s and then at a measuring rate of 0.1 mm/s, the depth of penetration being 0.3 mm. The value recorded for the hardness is that of the maximum peak.

In addition, this pasty compound is, at a temperature of 23° C., in the form of a liquid fraction and of a solid fraction. In other words, the starting melting temperature of the pasty compound is less than 23° C. The liquid fraction of the pasty compound, measured at 23° C., represents 9 to 97% by weight of the compound. This liquid fraction at 23° C. preferably represents between 15 and 85%, more preferably between 40 and 85%, by weight.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound to change from the solid state to the liquid state. The pasty compound is "in the solid state" when the whole of its mass is in the crystalline solid form. The pasty compound is "in the liquid state" when the whole of its mass is in the liquid form.

The enthalpy of fusion of the pasty compound is equal to the area under the curve of the thermogram obtained using a differential scanning calorimeter (DSC), such as the calorimeter sold under the name MDSC 2920 by TA Instrument, with a rise in temperature of 5 or 10° C. per minute, according to the ISO Standard 11357-3: 1999. The enthalpy of fusion of the pasty compound is the amount of energy necessary to change the compound from the solid state to the liquid state. It is expressed in J/g.

The enthalpy of fusion consumed at 23° C. is the amount of energy absorbed by the sample to change from the solid state to the state which it exhibits at 23° C., composed of a liquid fraction and of a solid fraction.

The liquid fraction of the pasty compound measured at 32° C. preferably represents from 30 to 100% by weight of the compound, preferably from 80 to 100%, more preferably from 90 to 100%, by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty compound is preferably chosen from synthetic compounds and compounds of plant origin. A pasty compound may be obtained by synthesis from starting materials of plant origin. Mention may be made especially, alone or as a mixture, of:

The pasty fatty substance is advantageously chosen from:
lanolin, and derivatives thereof, such as lanolin alcohol, oxyethylenated lanolins, acetylated lanolin, lanolin esters such as isopropyl lanolate, and oxypropylenated lanolins,
petroleum jelly, in particular the product whose INCI name is petrolatum and which is sold under the name Ultima White PET USP by the company Penreco,
polyol ethers chosen from polyalkylene glycol pentaerythrityl ethers, fatty alcohol ethers of sugars, and mixtures thereof, polyethylene glycol pentaerythrityl ether comprising five oxyethylene (5 OE) units (CTFA name: PEG-5 Pentaerythrityl Ether), polypropylene glycol pentaerythrityl ether comprising five oxypropylene (5 OP) units (CTFA name: PEG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil;
polymeric or non-polymeric silicone compounds;
polymeric or non-polymeric fluoro compounds;
vinyl polymers, especially:
olefin homopolymers and copolymers,
hydrogenated diene homopolymers and copolymers,
linear or branched oligomers, homopolymers or copolymers of alkyl(meth)acrylates preferably containing a $C_8$-$C_{30}$ alkyl group
oligomers, homopolymers and copolymers of vinyl esters containing $C_8$-$C_{30}$ alkyl groups
oligomers, homopolymers and copolymers of vinyl ethers containing $C_8$-$C_{30}$ alkyl groups
liposoluble polyethers resulting from the polyetherification between one or more $C_2$-$C_{100}$ and preferably $C_2$-$C_{50}$ diols,
esters (ie pasty fatty substance comprising at least one ester function); and/or
mixtures thereof.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Preferably, the pasty fatty substance comprises at least one ester function. Among the ester pasty fatty substances, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, preferably such as bis-diglyceryl polyacyladipate-2 sold under the brand name Softisan 649 by the company Sasol,
vinyl ester homopolymers containing $C_8$-$C_{30}$ alkyl groups, such as polyvinyl laurate (sold especially under the reference Mexomer PP buy the company Chimex) and arachidyl propionate sold under the brand name Waxenol 801 by Alzo,
phytosterol esters,
fatty acid triglycerides and derivatives thereof, for instance triglycerides of fatty acids, which are especially $C_{10}$-$C_{18}$, and partially or totally hydrogenated such as those sold under the reference Softisan 100 by the company Sasol,
pentaerythritol esters,
non-crosslinked polyesters resulting from polycondensation between a linear or branched $C_4$-$C_{50}$ dicarboxylic acid or polycarboxylic acid and a $C_2$-$C_{50}$ diol or polyol,
aliphatic esters of an ester resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid ester is chosen from:

a) partial or total esters of saturated linear mono-hydroxylated aliphatic monocarboxylic acids;
b) partial or total esters of unsaturated monohydroxylated aliphatic monocarboxylic acids;
c) partial or total esters of saturated monohydroxylated aliphatic polycarboxylic acids;
d) partial or total esters of saturated poly-hydroxylated aliphatic polycarboxylic acids;
e) partial or total esters of $C_2$ to $C_{16}$ aliphatic polyols that have reacted with a monohydroxylated or polyhydroxylated aliphatic monocarboxylic or poly-carboxylic acid, and mixtures thereof, esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (commercialized under the references Plandool G and Plandool G7), phytosteryl/isostearyl/stearyl/behenyl dimer dilinoleate (Plandool H or Plandool S), and mixtures thereof, esters obtained by allowing a monohydric alcohol having 1 to 34 carbon atoms to react with an ester which is obtained by reacting a dimer acid with an alcohol mixture of a dimer diol and a trihydric or higher hydric alcohol having 3 to 10 carbon atoms, by using 0.8 to 1.5, preferably 0.4 to 0.8, and even more preferably 0.2 to 3.5, molar equivalent(s) of the monohydric alcohol with respect to one molar equivalent of a carboxyl group remaining in the ester obtained from the dimer acid and the alcohol mixture.

The dimer acid can be obtained by standardized industrial processes. More particularly, the dimer acid can be obtained by dimerizing an unsaturated fatty acid with 11 to 22 carbon atoms, or a lower alcohol ester thereof with a clay catalyst or the like. The resulting dimer acid has a dibasic acid having about 36 carbon atoms as a main ingredient, and may contain a trimer acid and a monomer acid in amounts in accordance with the degree of purification. The dimers derived from vegetable fats and oils are preferable. As the aforementioned dimers, for example, PRIPOL 1006, PRIPOL 1009, PRIPOL 1015, and PRIPOL 1025 provided by Croda Inc., and the like, can be used.

The dimer diol is more particularly a product having a diol with about 36 carbon atoms as a main ingredient. The dimer diol is obtained by hydrogenating the aforementioned dimer acid and/or the lower alcohol ester thereof in the presence of a catalyst to form the diol having about 36 carbon atoms in which the carboxylic acid part of the dimer acid is an alcohol. The dimer diols derived from vegetable fats and oils are preferable. For example, PRIPOL 2033 provided by Croda Inc., can be used.

The trihydric or higher hydric alcohol having 3 to 10 carbon atoms is preferably selected from glycerol, diglycerol, trimethylolpropane, pentaerythritol, ditrimethylolpropane and dipentaerythritol.

The monohydric alcohol having 1 to 34 carbon atoms is more particularly selected from a linear saturated alcohol having 12 to 22 carbon atoms, a branched saturated alcohol having 8 to 22 carbon atoms, cholesterol and phytosterol. Preferably, the monohydric alcohol is a linear saturated monohydric alcohol having 16 or more carbon atoms, and is in the form of a paste. According to another embodiment, the monohydric alcohol is cholesterol or phytosterol. In addition, a double bond remains after the dimerization reaction. Therefore, a dimer acid in which hydrogenation is further carried out can be used.

Such products are for instance described in JP 2011-20933 filed in the name of Nippon Fine Chemical Co., Ltd.

mango butter, such as the product sold under the reference Lipex 203 by the company Aarhuskarlshamn, hydrogenated oils of plant origin such as hydrogenated castor oil isostearate (sold as (SALACOS HCIS (V-L) from NISSHIN OIL), hydrogenated soybean oil, hydrogenated coconut oil, hydrogenated rape seed oil, mixtures of hydrogenated plant oils such as the mixture of hydrogenated soybean, coconut, palm and rape seed plant oil, for example the mixture sold under the reference Akogel® by the company Aarhuskarlshamn (INCI name: Hydrogenated Vegetable Oil).

shea butter, in particular the product whose INCI name is *Butyrospermum parkii* Butter, such as the product sold under the reference Sheasoft® by the company Aarhuskarlshamn, hydrogenated rosinate esters, such as dilinoleyl dimers of hydrogenated rosinate (Lusplan DD-DHR or DD-DHR from Nippon Fine Chemical); and mixtures thereof.

Preferably, the pasty fatty substance is a hydrocarbon-based compound comprising at least one ester function.

Preferably, the pasty fatty substance, is chosen from hydrogenated castor oil isostearate (SALACOS HCIS (V-L) from par NISSHIN OIL), bis-behenyl/isostearyl/phytosteryl dimer dilinoleyl dimer dilinoleate, esters obtained by allowing a monohydric alcohol having 1 to 34 carbon atoms to react with an ester which is obtained by reacting a dimer acid with an alcohol mixture of a dimer diol and a trihydric or higher hydric alcohol having 3 to 10 carbon atoms, by using 0.8 to 1.5 molar equivalent(s) of the monohydric alcohol with respect to one molar equivalent of a carboxyl group remaining in the ester obtained from the dimer acid and the alcohol mixture (and for instance described in JP2011-20933), bis-diglyceryl polyacyladipate-2, hydrogenated castor oil dimer dilinoleate (Risocast-DA-L®, Risocast DA-H®, sold by Kokyu Alcohol Kogyo), polyvinyl laurate, mango butter, shea butter, hydrogenated soybean oil, hydrogenated coconut oil and hydrogenated rape seed oil, and mixtures thereof.

According to a particularly preferred embodiment of the invention, the composition for making up and/or caring for the skin and/or the lips, comprises, in a physiologically acceptable medium, at least one fatty phase comprising:

from 5 to 30% by weight of non volatile hydrocarbonated apolar oil(s), or mixture thereof, relative to the total weight of the composition, from 43 to 90% by weight of total content of non volatile silicone oil(s) relative to the total weight of the composition, wherein at least one of said non volatile silicone oil(s) is a non volatile phenylated silicon oil, preferably with no dimethicone part, and from 3 to 30% by weight of wax(es), or mixture thereof, relative to the total weight of the composition, at least a pasty compound chosen from (i) bis-behenyl/isostearyl/phytosteryl dimer dilinoleyl dimer dilinoleate; (ii) esters obtained by allowing a monohydric alcohol having 1 to 34 carbon atoms to react with an ester which is obtained by reacting a dimer acid with an alcohol mixture of a dimer diol and a trihydric or higher hydric alcohol having 3 to 10 carbon atoms, by using 0.8 to 1.5 molar equivalent(s) of the monohydric alcohol with respect to one molar equivalent of a carboxyl group remaining in the ester obtained from the dimer acid and the alcohol mixture; and preferably among (ii).

Fillers

A makeup and/or care composition according to the invention may also comprise one or more filler(s). According to a first embodiment, the composition is free of fillers.

According to a second preferred embodiment, the composition comprises at least one or more filler(s). The term "fillers" should be understood as meaning colorless or white, mineral or synthetic particles of any shape, which are insoluble in the medium of the composition, irrespective of the temperature at which the composition is manufactured. These fillers serve especially to modify the rheology or the texture of the composition.

The fillers may be mineral or organic and of any shape, platelet-shaped, spherical or oblong, irrespective of the crystallographic form (for example lamellar, cubic, hexagonal, orthorhombic, etc.). Mention may be made of talc, mica, silica, kaolin, clay, bentone, fumed silica particles, optionally hydrophilic- or hydrophobic-treated, polyamide (Nylon®) powder (Orgasol® from Atochem), poly-β-alanine powder and polyethylene powder, tetrafluoroethylene polymer (Teflon®) powder, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning) and silicone resin microbeads (for example Tospearls® from Toshiba), precipitated calcium carbonate, magnesium carbonate, magnesium hydrogen carbonate, hydroxyapatite, hollow silica microspheres (Silica Beads® from Maprecos), elastomeric polyorganosiloxane particles, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, and mixtures thereof.

They may also be particles comprising a copolymer, said copolymer comprising trimethylol hexyl lactone. In particular, it may be a copolymer polyurethane comprising trimethylol hexyl lactone and still more preferably a copolymer of hexamethylene diisocyanate/trimethylol hexyl lactone. Such particles are especially commercially available, for example, under the name Plastic Powder D-400® or Plastic Powder D-800® from the company Toshiki.

According to one preferred embodiment of the invention, the composition for making up and/or caring for the skin and/or the lips, comprises, in a physiologically acceptable medium, at least one fatty phase comprising from 5 to 30% by weight of non volatile hydrocarbonated apolar oil(s), or mixture thereof, relative to the total weight of the composition, from 43 to 90% by weight of total content of non volatile silicone oil(s) relative to the total weight of the composition, wherein at least one of said non volatile silicone oil(s) is a non volatile phenylated silicon oil, preferably with no dimethicone part, and from 3 to 30% by weight of wax(es), or mixture thereof, relative to the total weight of the composition, a filler advantageously chosen among copolymers comprising polyurethane, preferably polyurethane comprising trimethylol hexyl lactone and still more preferably a copolymer of hexamethylene diisocyanate/trimethylol hexyl lactone, According to this preferred embodiment, the quantity of the composition applied on the skin and/or on the lip, and preferably on the lips is advantageously increased; moreover the shine of the deposit as well as the colour transfer resistance are good.

More preferably, the composition according to this embodiment further comprises at least one pasty compound, advantageously chosen from (i) bis-behenyl/isostearyl/phytosteryl dimer dilinoleyl dimer dilinoleate; (ii) esters obtained by allowing a monohydric alcohol having 1 to 34 carbon atoms to react with an ester which is obtained by reacting a dimer acid with an alcohol mixture of a dimer diol and a trihydric or higher hydric alcohol having 3 to 10 carbon atoms, by using 0.8 to 1.5 molar equivalent(s) of the monohydric alcohol with respect to one molar equivalent of a carboxyl group remaining in the ester obtained from the dimer acid and the alcohol mixture, or their mixtures and preferably chosen from (ii).

According to a preferred embodiment, the composition according to the invention comprises at least silica, preferably hydrophobic treated silica.

According to one preferred embodiment, the composition comprises at least one filler, and in particular chosen from fumed silicas that have optionally been hydrophilic- or hydrophobic-treated, preferably hydrophobic-treated. Preferably, the composition comprises at least one filler known as Silica Dimethyl Silylate (according to the CTFA).

The hydrophobic groups may especially be dimethylsilyloxyl or polydimethylsiloxane groups, which are especially obtained by treating fumed silica in the presence of polydimethylsiloxane or dimethyldichlorosilane. Silicas thus treated are known as Silica Dimethyl Silylate according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

According to a particular embodiment, the composition according to the invention is free of "nanosilica", preferably free of hydrophobic treated silica of INCI name Silica Dimethyl Silylate. The term "nanosilica" means silica having a nanometric size, or at least a fraction of nanometric size.

Preferably, the composition contains between 0.01% and 25% by weight and in particular between 0.1% and 20% by weight of fillers relative to the total weight of the composition.

Preferably, when the composition is in liquid form, it comprises at least one filler, preferably chosen from silica, kaolin, bentone, fumed silica particles, which have preferably been hydrophobic-treated, lauroyllysine and starch.

Preferably, a composition according to the invention may comprise a filler chosen from:
- organomodified clays, which are preferably clays treated with compounds chosen especially from quaternary amines and tertiary amines. Organomodified clays that may be mentioned include organomodified bentonites, such as the product sold under the name Bentone 34 by the company Rheox, and organomodified hectorites such as the products sold under the names Bentone 27 and Bentone 38 by the company Rheox,
- hydrophobic fumed silica. Such silicas are sold, for example, under the references Aerosil R812® by the company Degussa and Cab-O-Sil TS-530® by the company Cabot, and under the references Aerosil R972® and Aerosil R974® by the company Degussa and Cab-O-Sil TS-610® and Cab-O-Sil TS-720® by the company Cabot.

The filler may be present in a content ranging from 0.1% to 5% by weight and better still from 0.4% to 3% by weight relative to the total weight of the composition.

Hydrophobic Silica Aerogel Particles

According to a preferred embodiment, the composition comprises may comprised at least hydrophobic silica aerogel particles. Such compound is a filler.

Preferably such compound is present when the composition is free of nanosilica and more particularly free of Silica Dimethyl Silylate.

Preferably the hydrophobic silica aerogel particles may be present in a content ranging from 0.1% to 15% by weight and better still from 0.1% to 10% by weight, relative to the total weight of the composition.

Preferably the hydrophobic silica aerogel particles may be present in a content ranging from 0.1% to 6% by weight and better still from 0.2% to 4% by weight, relative to the total weight of the composition.

According to this embodiment, the composition may comprise at least a additional filler, such as those described before for example.

Preferably, the composition according to the invention comprises at least hydrophobic silica aerogel particles, when the composition is free of nanometric silica particles as described before, such as Silica Dimethyl Silylate.

Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G W., Sol-Gel Science: New York: Academic Press, 1990.

The hydrophobic silica aerogel particles that may be used in the present invention have a specific surface area per unit of mass ($S_M$) ranging from 500 to 1500 $m^2/g$, preferably from 600 to 1200 $m^2/g$ and better still from 600 to 800 $m^2/g$, and a size expressed as the mean volume diameter (D[0.5]), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles that may be used in the present invention have a size expressed as the mean volume diameter (D[0.5]) ranging from 1 to 30 μm, preferably from 5 to 25 μm, better still from 5 to 20 μm and even better still from 5 to 15 μm.

The specific surface area per unit of mass may be determined via the BET (Brunauer-Emmett-Teller) nitrogen absorption method described in the *Journal of the American Chemical Society*, vol. 60, page 309, February 1938 and corresponding to the international standard ISO 5794/1 (appendix D). The BET specific surface area corresponds to the total specific surface area of the particles under consideration.

The size of the hydrophobic silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter.

This theory is especially described in the publication by Van de Hulst, H. C., "Light Scattering by Small Particles," Chapters 9 and 10, Wiley, New York, 1957.

According to one advantageous embodiment, the hydrophobic silica aerogel particles used in the present invention have a specific surface area per unit of mass ($S_M$) ranging from 600 to 800 $m^2/g$ and a size expressed as the mean volume diameter (D[0.5]) ranging from 5 to 20 μm and better still from 5 to 15 μm.

The hydrophobic silica aerogel particles used in the present invention may advantageously have a tamped density ρ ranging from 0.04 $g/cm^3$ to 0.10 $g/cm^3$ and preferably from 0.05 $g/cm^3$ to 0.08 $g/cm^3$. In the context of the present invention, this density, known as the tamped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in $cm^3$ and m in g).

According to one embodiment, the hydrophobic silica, particles that may be used in the present invention have a specific surface area per unit of volume $S_V$ ranging from 5 to 60 $m^2/cm^3$, preferably from 10 to 50 $m^2/cm^3$ and better still from 15 to 40 $m^2/cm^3$.

The specific surface area per unit of volume is given by the relationship:
$S_V = S_M \cdot \rho$; where ρ is the tamped density expressed in $g/cm^3$ and $S_M$ is the specific surface area per unit of mass expressed in $m^2/g$, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The oil-absorbing capacity measured at the wet point, noted Wp, corresponds to the amount of water that needs to be added to 100 g of particle in order to obtain a homogeneous paste.

It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount m=2 g of powder is placed on a glass plate, and the oil (isononyl isononanoate) is then added dropwise.

After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The hydrophobic silica aerogel particles that may be used according to the present invention are preferably of silylated silica type (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogels particles that have been surface-modified by silylation, reference may be made to document U.S. Pat. No. 7,470,725.

Use will be made in particular of hydrophobic silica aerogels particles surface-modified with trimethylsilyl groups.

As hydrophobic silica aerogel particles that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 $m^2/g$.

Mention may also be made of the aerogels sold by the company Cabot under the references Aerogel TLD 201, Aerogel OGD 201, Aerogel TLD 203, and ENOVAAEROGEL MT 1100.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 $m^2/g$ (oil uptake equal to 1080 ml/100 g).

Advantageously, the hollow particles in accordance with the invention are at least partly formed from hydrophobic silica aerogel particles, preferably those with a specific surface area per unit of mass ($S_M$) ranging from 500 to 1500 $m^2/g$ and preferably from 600 to 1200 $m^2/g$, and a size expressed as the mean volume diameter (D[0.5]), ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

The use of hydrophobic silica aerogel particles, also advantageously makes it possible to improve the stability of the composition.

Dextrin Ester

The composition according to the invention may comprise at least an ester of dextrin, preferably an ester of dextrin and a fatty acid, preferably a $C_{12}$ à $C_{24}$.fatty acid.

Preferably, the dextrin ester is an ester of dextrin and a $C_{14}$-$C_{18}$ fatty acid.

Preferably, the dextrin ester is dextrin palmitate, for example such as those commercialized under the references Rheopearl TL® or Rheopearl KL® by the society CHIBA FLOUR.

A composition according to the invention may comprise a content of dextrin ester ranging from 0.1% to 15% by weight and preferably from 0.5% to 10% by weight, relative to the total weight of the composition.

A composition according to the invention may comprise a content of dextrin ester ranging from 1% to 8% by weight and preferably from 2% to 6% by weight, relative to the total weight of the composition. According to a preferred embodiment, the composition according to the invention, the composition is free from dextrin ester.

Dyestuffs

The compositions according to the invention may preferably comprise at least one dyestuff (also known as a colouring agent), which may be chosen from water-soluble or liposoluble dyes, pigments and nacres, and mixtures thereof.

The composition according to the invention may also comprise one or more dyestuffs chosen from water-soluble dyes and pulverulent dyestuffs, for instance pigments, nacres and glitter flakes that are well known to those skilled in the art.

The dyestuffs may be present in the composition in a content ranging from 0.01% to 30% by weight, relative to the weight of the composition, preferably from 0.1% to 20% by weight.

The term "pigments" should be understood as meaning white or coloured, mineral or organic particles that are insoluble in an aqueous solution, which are intended to colour and/or opacify the resulting film. The pigments may be present in a proportion of from 0.01% to 30% by weight, especially from 0.1% to 25% by weight and in particular from 0.2% to 15% by weight relative to the total weight of the cosmetic composition.

As mineral pigments that may be used in the invention, mention may be made of titanium oxide, zirconium oxide or cerium oxide, and also zinc oxide, iron oxide or chromium oxide, ferric blue, manganese violet, ultramarine blue and chromium hydrate.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

The dyestuff may also comprise a pigment with a structure that may be, for example, of silica microsphere type containing iron oxide. An example of a pigment having this structure is the product sold by the company Miyoshi under the reference PC Ball PC-LL-100 P, this pigment consisting of silica microspheres containing yellow iron oxide.

Among the organic pigments that may be used in the invention, mention may be made of carbon black, pigments of D&C type, lakes based on cochineal carmine or on barium, strontium, calcium or aluminium, or alternatively the diketopyrrolopyrroles (DPP) described in documents EP-A-542 669, EP-A-787 730, EP-A-787 731 and WO-A-96/08537.

The term "nacres" should be understood as meaning coloured particles of any form, which may or may not be iridescent, especially produced by certain molluscs in their shell, or alternatively synthesized, and which have a colour effect via optical interference.

The nacres may be chosen from nacreous pigments such as titanium mica coated with an iron oxide, mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Tunica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or tint.

As illustrations of nacres that may be used in the context of the present invention, mention may be made especially of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Tunica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

The term "dyes" should be understood as meaning compounds that are generally organic, which are soluble in fatty substances such as oils or in an aqueous-alcoholic phase.

The cosmetic composition according to the invention may also comprise water-soluble or liposoluble dyes. The liposoluble dyes are, for example, Sudan red, DC Red 17, DC Green 6, β-carotene, Sudan brown, DC Yellow 11, DC Violet 2, DC Orange 5 and quinoline yellow. The water-soluble dyes are, for example, beetroot juice or methylene blue.

The cosmetic composition according to the invention may also contain at least one material with a specific optical effect as dyestuff.

This effect is different from a simple conventional hue effect, i.e. a unified and stabilized effect as produced by standard dyestuffs, for instance monochromatic pigments. For the purposes of the invention, the term "stabilized" means lacking an effect of variability of the colour as a function of the angle of observation or alternatively in response to a temperature change.

For example, this material may be chosen from particles with a metallic tint, goniochromatic coloring agents, diffracting pigments, thermochromic agents, optical brighteners, and also fibres, especially interference fibres. Needless to say, these various materials may be combined so as to afford the simultaneous manifestation of two effects, or even of a novel effect in accordance with the invention.

Aqueous Phase

A composition according to the invention may also comprise an aqueous phase, which may represent 0.01% to 50% by weight, especially 0.1% to 30% by weight or even 1% to 20% by weight relative to the total weight of the composition. This aqueous phase may be formed essentially from water, or may comprise a mixture of water and of water-miscible solvent (miscibility in water of greater than 50% by weight at 25° C.) chosen especially from monoalcohols containing 1 to 5 carbon atoms such as ethanol, isopropanol, glycols containing 2 to 8 carbon atoms such as propylene glycol, ethylene glycol, 1,3-butylene glycol, dipropylene glycol, $C_3$-$C_4$ ketones and $C_2$-$C_4$ aldehydes, and mixtures thereof.

However, as stated above, advantageously, the compositions according to the invention are anhydrous. The term "anhydrous" especially means that water is preferably not deliberately added to the compositions, but may be present in trace amounts in the various compounds used in the compositions.

Additive(s)

A makeup and/or care composition according to the invention may also comprise at least one agent usually used in cosmetics, chosen, for example, from reducing agents, thickeners, film-forming agents that are especially hydrophobic, silicone elastomers, softeners, antifoams, moisturizers, UV-screening agents, ceramides; cosmetic active agents; peptizers, fragrances, proteins, vitamins, propellants, hydrophilic or lipophilic, film-forming or non-film-forming polymers; lipophilic or hydrophilic gelling agents. The above additives are generally present in an amount for each of them of between 0.01% and 10% by weight relative to the total weight of the composition. Needless to say, a person skilled in the art will take care to select the constituents of the composition such that the advantageous properties associated with the invention are not, or are not substantially, adversely affected.

Usual Additional Cosmetic Ingredient

A composition used according to the invention may also comprise any usual cosmetic ingredient, which may be chosen especially from antioxidants, film-forming polymers, fragrances, preserving agents, emollients, moisturizers, neutralizers, sunscreens, sweeteners, vitamins, free-radical scavengers and sequestrants, and mixtures thereof.

The amounts of each of these various ingredients are those conventionally used in the fields under consideration, and range, for example, from 0.01% to 10% by weight relative to the total weight of the composition.

Needless to say, a person skilled in the art will take care to select the optional additional ingredients and/or the amount thereof such that the advantageous properties of the composition according to the invention are not, or are not substantially, adversely affected by the envisaged addition.

A composition in accordance with the invention may be in liquid form or in solid form.

According to a first preferred embodiment, the composition is in solid form. In particular, it may be a cosmetic product chosen from a lip balm and/or a lipstick. This product may preferably be in the form of a stick or cast in a dish.

According to one embodiment, it is a lipstick or a lip balm in stick form.

A composition according to the invention may constitute a liquid lipstick for the lips, a body makeup product, a facial or body care product or an antisun product.

According to second embodiment, a composition of the invention is in liquid form. As illustrations of liquid formulations, mention may be made especially of lip glosses.

As stated previously, the composition according to the invention is homogeneous and stable and gives access to a deposit on the skin or the lips that has good cosmetic properties, in particular in terms of gloss, comfort (thickness deposit) and absence of transfer of the deposit. In particular, compositions according to the invention enable the obtention of a deposit exhibits no color transfer, in particular on a cup while drinking for a lip product, and when the composition contains one or more colouring agent(s).

EXAMPLES

In the description and in the examples that follow, unless otherwise mentioned, the percentages are weight percentages and the ranges of values given in the form "between . . . and . . . " include the stated lower and upper limits.

Unless otherwise mentioned, the values in the example below are expressed as % by weight relative to the total weight of the composition.

The examples below are presented as non-limiting illustrations of the field of the invention.

Examples 1 to 5 of Cosmetic Formulae of Solid Lip Product Type

Lipstick

Six solid lip makeup formulae having the following compositions were prepared (lipsticks) (the percentages indicated are weight percentages). Formulae 1, 2 and 3 illustrate the invention, and formulae 4 and 5 are comparative compositions outside the invention.

| INCI name and commercial references | Formula 1 according to the invention (% in weight) | Formula 2 according to the invention (% in weight) | Formula 3 according to the invention (% in weight) | Comparative Formula 4 not belonging to the invention (% in weight) | Comparative Formula 5 Not belonging to the invention (% in weight) |
|---|---|---|---|---|---|
| TRIMETHYL PENTAPHENYL TRISILOXANE (DOW CORNING PH-1555 HRI COSMETIC FLUID from Dow corning) | 35 | 45 | 35 | 35 | 0 |
| DIPHENYLSILOXY PHENYL TRIMETHICONE (KF-56A from Shin Etsu) | 14 | 14 | 0 | 14 | 0 |
| HYDROGENATED POLYISOBUTENE (PARLEAM V from NOF Corporation) | 20 | 20 | 20 | 0 | 20 |
| GLYCERYL ISOSTEARATE (PECEOL ISOSTEARIQUE from Fattefosse) | 0 | 0 | 0 | 20 | 0 |
| POLYETHYLENE (PERFORMALENE 500-L POLYETHYLENE from New Phase Technologies) | 6 | 6 | 6 | 6 | 6 |
| OZOKERITE (OZOKERITE WAX SP 1020 P from STRAHL & PITSCH) | 1 | 1 | 1 | 1 | 1 |
| PENTAERYTHRITYL TETRAISO-STEARATE (CRODAMOL PTIS-LQ-(MH) from CRODA) | 3.01 | 3.01 | 3.01 | 3.01 | 3.01 |
| BLUE 1 LAKE | 0.2 | 0.2 | 0.2 | 0.2 | 0.2 |
| YELLOW 5 LAKE | 0.85 | 0.85 | 0.85 | 0.85 | 0.85 |
| RED 7 | 0.47 | 0.47 | 0.47 | 0.47 | 0.47 |
| TITANIUM DIOXIDE | 0.2 | 0.2 | 0.2 | 0.2 | 0.2 |
| IRON OXIDES | 0.97 | 0.97 | 0.97 | 0.97 | 0.97 |
| MICA (and) TITANIUM DIOXIDE | 4.3 | 4.3 | 4.3 | 4.3 | 4.3 |

-continued

| INCI name and commercial references | Formula 1 according to the invention (% in weight) | Formula 2 according to the invention (% in weight) | Formula 3 according to the invention (% in weight) | Comparative Formula 4 not belonging to the invention (% in weight) | Comparative Formula 5 Not belonging to the invention (% in weight) |
|---|---|---|---|---|---|
| Dimethicone (XIAMETER PMX-200 SILICONE FLUID 350CS from Dow Corning) | 5 | 0 | 5 | 5 | 5 |
| Dimethicone (XIAMETER PMX-200 SILICONE FLUID 100CS from Dow Corning) | 5 | 0 | 19 | 5 | 54 |
| ISOHEXADECANE | 4 | 4 | 4 | 4 | 4 |
| TOTAL: | 100 | 100 | 100 | 100 | 100 |

Preparation Process

The compositions of Examples 1 to 5 were obtained according to the following protocol:

In a first stage, the fillers, pigments and/or active agents of the fatty phase were ground in a three-roll mill in part of the oily phase (in PENTAERYTHRITYLTETRAISOSTEARATE)

In parallel, the waxes and the rest of the liposoluble ingredients are introduced into a heating pan and mixed in the heating pan at a temperature of about 100° C. with Rayneri blending until a homogeneous mixture was obtained. The ground pigmentary material was then incorporated into the mixture, along with the nacres, if present, and stirring was continued until the mixture was homogeneous.

Finally, the compositions were poured into moulds pre-heated to 40° C., to produce sticks 11.5 mm in diameter. The whole was then left to cool in a freezer for about one hour, and then placed at room temperature for 24 hours.

Evaluation

The hardness of compositions 1 to 5 at 20° C. was evaluated according to the protocol described previously. The measured values of the hardness of the compositions are listed in the table before.

For the comparative composition 5, it was not possible to obtain a stick and to measure the value of the hardness, because while mixing at high temperature, a phase separation has occurred.

Each of the compositions obtained was placed for 72 hours at 24° C. and at 47° C. in order to evaluate the stability of the composition. More particularly, it is observed if the compositions remain homogenous (no phase separation and/or no exudation for example) and if the stick remain unchanged.

Each of the compositions was then applied to the lips in order to evaluate the application properties and the characteristics of the deposit obtained; and more particularly the easiness to apply (quantity of composition applied and glidance on application), the shine of the deposit, and the Color transfer resistance, particularly on a cup.

The color transfer resistance is evaluated after applying the composition and rubbing the lower and the upper lips together for 5 seconds, and by applying the lips on a white pottery cup 5 minutes after applying the compositions on the lips.

The shine is evaluated according to the following protocol:

The composition is applied on Bio Skin (Beaulax) by fixed number of strokes and measure the shine by gloss meter (GM-268, MINOLTA) on the condition of 60 degree illuminating angle and 60 degree acceptance angle.

The deposit amount is measured by its weight loss after application on the Bio Skin.

The results obtained are the following:

| | Formula 1 according to the invention (% in weight) | Formula 2 according to the invention (% in weight) | Formula 3 according to the invention (% in weight) | Comparative Formula 4 not belonging to the invention (% in weight) | Comparative Formula 5 not belonging to the invention (% in weight) |
|---|---|---|---|---|---|
| Aspect of the composition | Homogeneous Stick | Homogeneous Stick | Homogeneous Stick | Homogeneous Stick | Non Homogeneous No Stick could be obtained |
| HARDNESS (N · m-1) | 51.1 | 53.7 | 56.3 | 44.3 | Could not be measured |
| Stability after 72 hours at 24° C. | Yes: Still homogeneous and stick not collapsing | Yes: Still homogeneous and stick not collapsing | Yes: Still homogeneous and stick not collapsing | Yes: Still homogeneous and stick not collapsing | No: composition not homogeneous (phase separation) |

|  | Formula 1 according to the invention (% in weight) | Formula 2 according to the invention (% in weight) | Formula 3 according to the invention (% in weight) | Comparative Formula 4 not belonging to the invention (% in weight) | Comparative Formula 5 not belonging to the invention (% in weight) |
| --- | --- | --- | --- | --- | --- |
| Stability after 72 hours at 47° C. | Yes: Still homogeneous and stick not collapsing | Yes: Still homogeneous and stick not collapsing | Yes: Still homogeneous and stick not collapsing | Yes: Still homogeneous and stick not collapsing | No: composition not homogeneous (phase separation) |
| Quantity of the deposit (mg) | 13.1 | 11.9 | 12.8 | 12.2 | No evaluation was possible |
| Gliding | Good | Good | Moderately good | Very good | No evaluation was possible |
| Shine of the deposit | Good | Good | Moderately good | Moderately good | No evaluation was possible |
| Color transfer resistance | Good | Very Good | Very Good | Bad | No evaluation was possible |

Composition 1, 2, 3, and 4 are solid enough as not to fracture or crack when it is applied to the lips or on a blenderm. Furthermore, compositions 1, 2, 3, and 4 are stable over time, without exudation or collapse, in particular after 1 month at 24° C., and 47° C. Beside, none of the obtained sticks is collapsing while being placed at 47° C., for compositions 1, 2, 3 and 4.

On contrary, comparative composition 5 containing no non volatile phenylated silicone oil, is not homogenous (phase separation while mixing at high temperature) and is not hard enough to obtain a stick. Composition 5 not cosmetically acceptable: is to pasty and unhomogeneous to enable forming a homogenous acceptable deposit. No evaluation of the properties of shine and color transfert resistance could be realised.

Composition 1 and 3, according to the invention, comprising a non volatile hydrocarbonated apolar oil, a non volatile non phenylated dimethicone oil and a non volatile phenylated silicone oil are easy to apply on the lips (good and homogenous erosion (fondant, creamy sensation) of the stick while applying, and good or acceptable glide). The deposit obtained on the lips is thick, comfortable, and homogeneous. Beside, compositions 1 and 3 according to the invention enable forming a deposit having good or very good color transfer resistance on a cup. At the same time, these composition 1 and 3 enable forming a deposit having a good level of shine or a moderately good level of shine, but still acceptable.

Composition 2, according to the invention, comprising a non volatile hydrocarbonated apolar oil and a non volatile phenylated silicone oil (but no non volatile non phenylated dimethicone oil) is easy to apply on the lips (good and homogenous erosion; fondant, creamy sensation of the stick while applying, and good or acceptable glide). The deposit obtained on the lips for composition 2 according to the invention enable forming a deposit having a moderately good or very good color transfer resistance on a cup. Beside the deposit obtained on the lips is thick, comfortable, and homogeneous. At the same time, this composition 2 enables forming a deposit having a good level of shine.

Comparative composition 4 comprising a non volatile non phenylated dimethicone oil and a non volatile phenylated silicone oil but no non volatile hydrocarbonated apolar oil (the apolar oil of compositions 1 has been replaced weight by weight by glyceryl isostearate) has a bad color transfer resistance. Therefore, thought it is easy to apply and the deposit has a good level of shine, this composition does not meet the objective of the invention.

Comparative composition 5 comprising a non volatile hydrocarbonated apolar oil, a non volatile non phenylated silicone oil but no non volatile phenylated dimethicone oil (the non volatile phenylated silicone oil of composition 1 has been replaced weight by weight by non volatile non phenylated silicone oil) is not homogenous. It was not possible to obtain a stick (composition not hard enough), and the composition was to pasty to be applied in an acceptable manner (not homogenous deposit at all) and to be evaluated in terms of shine and color transfer resistance.

Example 6 of Cosmetic Formulae of Solid Lip Product Type

Lipstick

The following solid lip makeup formulae having the following composition was prepared (lipsticks) (the percentages indicated are weight percentages). Formula 6 illustrate the invention is based on the previous formula 2 wherein 10% by weight of the hydrogenated polyisobutene has been replaced by 10% of a fatty pasty compound.

| INCI name and commercial references | Formula 6 according to the invention (% in weight) |
| --- | --- |
| TRIMETHYL PENTAPHENYL TRISILOXANE (DOW CORNING PH-1555 HRI COSMETIC FLUID from Dow corning) | 45 |
| DIPHENYLSILOXY PHENYL TRIMETHICONE (KF-56A from Shin Etsu) | 14 |
| HYDROGENATED POLYISOBUTENE (PARLEAM V from NOF Corporation) | 10 |
| POLYETHYLENE (PERFORMALENE 500-L POLYETHYLENE from New Phase Technologies) | 6 |
| OZOKERITE (OZOKERITE WAX SP 1020 P from STRAHL & PITSCH) | 1 |
| BIS-BEHENYL/ISOSTEARYL/PHYTOSTERYL DIMER DILINOLEYL DIMER DILINOLEATE (PLANDOOL G from Nippon Fine Chemical) | 10 |
| PENTAERYTHRITYL TETRAISOSTEARATE (CRODAMOL PTIS-LQ-(MH) from CRODA) | 3.01 |
| BLUE 1 LAKE | 0.2 |
| YELLOW 5 LAKE | 0.85 |
| Red 7 | 0.47 |

| INCI name and commercial references | Formula 6 according to the invention (% in weight) |
|---|---|
| TITANIUM DIOXIDE | 0.2 |
| IRON OXIDES | 0.97 |
| MICA (and) TITANIUM DIOXIDE | 4.3 |
| ISOHEXADECANE | 4 |
| TOTAL: | 100 |

Composition 6 has been prepared and evaluated in the same manner as described before.

The results obtained are the following:

| PROPERTIES | Formula 6 according to the invention (% in weight) |
|---|---|
| Aspect of the composition | Homogeneous stick |
| HARDNESS (N · m−1) | 73.3 |
| Stability after 72 hours at 24° C. | Yes: Still homogeneous and stick not collapsing |
| Stability after 72 hours at 47° C. | Yes: Still homogeneous and stick not collapsing |
| Quantity of the deposit (mg) | 13.1 |
| Gliding | Good |
| Shine of the deposit | Very Good |
| Color transfer resistance | Good |

Composition 6, according to the invention, comprising a non volatile hydrocarbonated apolar oil, a non volatile non phenylated dimethicone oil and a non volatile phenylated silicone oil is easy to apply on the lips (good and homogenous erosion (fondant, creamy sensation) of the stick while applying, and good glide). The deposit obtained on the lips is thick, comfortable, and homogeneous. Beside, composition 6 according to the invention enables forming a very shiny deposit having a good color transfer resistance on a cup.

Examples 7 to 9 of Cosmetic Formulae of Solid Lip Product Type

Lipstick

The following composition according to the invention was prepared according to the preceding methods (the percentages indicated are weight percentages).

| INCI and commercial references | composition 7 | composition 8 | composition 9 | composition 10 |
|---|---|---|---|---|
| Trimethyl pentaphenyl trisiloxane (DOW CORNING PH-1555 HRI COSMETIC FLUID from Dow corning) | 45 | 45 | 35 | 35 |
| Diphenylsiloxy phenyl trimethicone (KF-56A from Shin Etsu) | 14 | 14 | 14 | 14 |
| Hydrogenated polyisobutene (PARLEAM V from NOF Corporation) | 10 | 9 | 10 | 10 |
| Polyethylene (PERFORMALENE 500-L POLYETHYLENE from New Phase Technologies) | 6 | 6 | 6 | 6 |
| Ozokerite (OZOKERITE WAX SP 1020 P from STRAHL & PITSCH) | 1 | 1 | 1 | 1 |
| Behenyl/dimer dilinoleyl/glyceryl/phytosteryl dimer dilinoleate (*) | 10 | 10 | 10 | 0 |
| Bis-behenyl/isostearyl/phytosteryl/ dimer dilinoleyl/dinoleate (Plandool-G7 from Nippon Fine Chemicals) | 0 | 0 | 0 | 10 |
| PentaerythritylTetraisostearate (CRODAMOL PTIS-LQ-(MH) from CRODA) | 3.01 | 3.01 | 3.01 | 3.01 |
| Blue 1 lake | 0.2 | 0.2 | 0.2 | 0.2 |
| Yellow 5 lake | 0.85 | 0.85 | 0.85 | 0.85 |
| Red 7 | 0.47 | 0.47 | 0.47 | 0.47 |
| Titanium dioxide | 0.2 | 0.2 | 0.2 | 0.2 |
| Iron oxides | 0.97 | 0.97 | 0.97 | 0.97 |
| Mica (and) titanium dioxide | 4.3 | 4.3 | 4.3 | 4.3 |
| HDI/trimethylol hexyllactone crosspolymer and silicic anhydrate (Plastic Powder from Toshiki Pigment Co) | 0 | 1 | 0 | 0 |
| Dimethicone (XIAMETER PMX-200 SILICONE FLUID 350CS from Dow Corning) | 0 | 0 | 5 | 5 |

| INCI and commercial references | composition 7 | composition 8 | composition 9 | composition 10 |
|---|---|---|---|---|
| Dimethicone (XIAMETER PMX-200 SILICONE FLUID 100CS from Dow Corning) | 0 | 0 | 5 | 5 |
| Isohexadecane | 4 | 4 | 4 | 4 |
| | 100 | 100 | 100 | 100 |

(*) Synthesis of the behenyl/dimer dilinoleyl/glyceryl/phytosteryl dimer dilinoleate A hydrogenated dimer acid (Pripol 1006 from Croda Inc.; 1100 g (1.902 mol)), a dimer diol (Pripol 2033, from Croda Inc.; 20.9 g (0.038 mol)), glycerin (74.4 g (0.808 mol)), behenyl alcohol (Stenol 1822A from Cognis; 375.9 g (1.179 mol)) and phytosterol (from ADM, 128.3 g (0.314 mol)) were placed in a reactor equipped with a stirrer, a thermometer and a gas introducing tube.

The mixture was heated to 210° C. to 220° C. under a nitrogen stream to carry out an esterification reaction for 41 hours while water produced during the reaction was distilled off.

Thereby, 1618 g of the target ester was obtained (yield: 99.2%).

The obtained ester was a pale yellow paste (Gardner color: 1 or less; acid value: 4.0; saponification value: 133.6; hydroxyl value: 6.8).

Evaluation

The same evaluation methods as detailed in the preceding examples were used.

The properties of the composition are indicated in the table below:

| | Composition 7 | Composition 8 | Composition 9 | Composition 10 |
|---|---|---|---|---|
| Quantity of the deposit (mg) | 12.5 | 15.6 | 9.6 | 10 |
| Shine of the deposit | Very good | Very good | Good | Good |
| Gliding | Good | Good | Good | Good |
| Color transfer resistance | Very good | Very good | Good | Good |

Moreover, the compositions were homogeneous and the feeling of moisturizing of the lips was very good.

The invention claimed is:

1. A solid cosmetic composition for making up and/or caring for the skin and/or the lips, comprising, in a physiologically acceptable medium. at least one fatty phase comprising:
   at least one non-volatile hydrocarbonated apolar oil, wherein the total amount of non-volatile hydrocarbonated apolar oil ranges from about 5% to about 30% by weight, relative to the total weight of the composition;
   at least one non-volatile phenylated silicone oil chosen from trimethyl pentaphenyl trisiloxane, diphenylsiloxy phenyltrimethicone, or mixtures thereof, wherein the total amount of non-volatile phenylated silicone oil ranges from 43% to 90% by weight, relative to the total weight of the composition;
   at least one wax, wherein the total amount of wax ranges from about 3% to about 30% by weight, relative to the total weight of the composition; and
   at least one volatile hydrocarbon oil,
   wherein the cosmetic composition is anhydrous, wherein the total amount of water is less than 1% by weight, relative to the total weight of the composition; and
   wherein the solid cosmetic composition is capable of providing improved color development and improved color transfer resistance.

2. The solid cosmetic composition of claim 1, wherein the at least one non-volatile hydrocarbonated apolar oil is chosen from polybutene, hydrogenated polybutene, polyisobutene, hydrogenated polyisobutene, polydecene, hydrogenated polydecene, or mixtures thereof.

3. The solid cosmetic composition of claim 1, wherein the total amount non-volatile hydrocarbonated apolar oil ranges from about 5 to about 25% by weight, relative to the total weight of the composition.

4. The solid cosmetic composition of claim 1, wherein the total amount of non-volatile phenylated silicone oil ranges from about 45 to about 70% by weight, relative to the total weight of the composition.

5. The solid cosmetic composition of claim 1, wherein the solid cosmetic composition further comprises:
   a) phenyl silicone oils of formula (I)

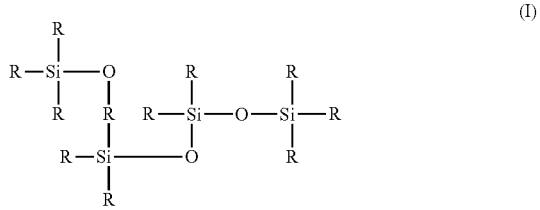

wherein R is independently chosen from methyl groups or phenyl groups,
wherein at least one R represents a phenyl group;
b) phenyl silicone oils of formula (II):

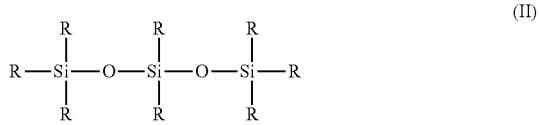

wherein R is independently chosen from methyl groups or phenyl groups,
wherein at least one R represents a phenyl group;
c) phenyl silicone oils of formula (III):

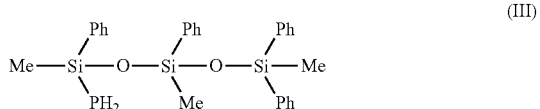

wherein Me represents methyl and Ph represents phenyl;

d) phenyl silicone oils of formula (IV):

$$\text{X—Si(Me)(Me)—[O—Si(Me)(Me)]}_y\text{—O—Si(Me)(Me)—X} \quad (IV)$$

wherein Me represents methyl. y ranges from 1 to 1000, and X represents —CH$_2$—CH(CH$_3$)(Ph);

e) phenyl silicone oils of formula (V):

$$\text{Me—Si(Me)(Me)—[O—Si(Me)(Me)]}_y\text{—[O—Si(OR')(Ph)]}_z\text{—O—Si(CH}_3)_3 \quad (V)$$

wherein Me represents methyl and Ph represents phenyl, R' represents SiMe$_3$, y is 0 or ranges from 1 to 1000, and z ranges from 1 to 1000;

f) phenyl silicone oils of formula (VI), and mixtures thereof:

(VI)

[structure with R$_1$ to R$_{10}$, indices p, q, n, m]

wherein:
R$_1$ to R$_{10}$ are independently chosen from saturated or unsaturated, linear, cyclic or branched C$_1$-C$_{30}$ hydrocarbon-based radicals,
m, n, p and q are independently chosen from integers ranging from 0 and 900, wherein the sum m+n+q is other than 0;

g) phenyl silicone oils of formula (VII), and mixtures thereof:

(VII)

[structure with R1, R2, R3, R4, index p and n, H$_3$C and phenyl groups]

[continued structure with phenyl, R5, R6, Si(CH$_3$)$_3$, index m]

wherein:
R$_1$ to R$_6$ are independently chosen from saturated or unsaturated, linear, cyclic or branched C$_1$-C$_{30}$ hydrocarbon-based radicals;
m, n and p are independently chosen from integers between 0 and 100,
wherein the sum n+m is between 1 and 100;

h) phenyl silicone oils of formula (IX), and mixtures thereof:

(IX)

$$\text{X—Si(R1)(R2)—[O—Si(R3)(R4)]}_n\text{—[O—Si(R5)(R6)]}_p\text{—O—Si(R1)(R2)—X}$$

wherein:
R$_1$, R$_2$, R$_5$ and R$_6$ are independently chosen from alkyl radicals containing 1 to 6 carbon atoms;
R$_3$ and R$_4$ are independently chosen from alkyl radicals containing from 1 to 6 carbon atoms or an aryl radical wherein at least one of R$_3$ and R$_4$ is a phenyl radical;
X is an alkyl radical containing from 1 to 6 carbon atoms, a hydroxyl radical or a vinyl radical;
n and p are independently chosen from an integer greater than or equal to 1, chosen so as to give the oil a weight-average molecular mass of less than 200 000 glmol;
i) or mixtures thereof.

6. The solid cosmetic composition of claim 1, wherein the solid cosmetic composition further comprises:
Tetramethyl Tetraphenyl Trisiloxane;
diphenylsiloxyphenyldimethicone;
phenyldimethicones;
phenyltrimethylsiloxydiphenylsiloxanes;
diphenyl dimethicones;
diphenylmethyldiphenyltrisiloxanes;
2-phenylethyl trimethylsiloxysilicates;
or mixtures thereof.

7. The solid cosmetic composition of claim 1, wherein the ratio of non-volatile phenylated silicone oils having at least one dimethicone part to non-volatile phenylated silicone oils with no dimethicone part is less than 0.02.

8. The solid cosmetic composition of claim 1, further comprising at least one non-volatile, non-phenylated silicone oil.

9. The solid cosmetic composition of claim 8, wherein:
the at least one non-volatile, non-phenylated silicone oil is a non-volatile, non-phenylated dimethicone oil, and
the weight ratio of the total non-volatile phenylated silicone oil to the total non-volatile, non-phenylated dimethicone oil is greater than or equal to 1.

10. The solid cosmetic composition of claim 1, wherein the composition is free from non-volatile silicone oil having a dimethicone part.

11. The solid cosmetic composition of claim 1, wherein the weight ratio of the non-volatile hydrocarbonated apolar oil to the non-volatile phenylated silicone oil ranges from about 0.1 to about 0.5.

12. The solid cosmetic composition of claim 1, wherein the at least one wax is chosen from apolar waxes.

13. The solid cosmetic composition of claim 1, wherein the wax is present in an amount ranging from about 3% to about 20%, by weight, relative to the total weight of the composition.

14. The solid cosmetic composition of claim 1, further comprising at least one additional compound, chosen from hydrocarbonated polar oils, volatile oils fatty pasty compounds, fillers, coloring agents, or mixtures thereof.

15. The solid cosmetic composition of claim 1, wherein the composition has a hardness value ranging from about 60 and about 200 $Nm^{-1}$.

16. A method for making up and/or caring for the skin and/or the lips, comprising, applying to the skin and/or the lips a cosmetic composition comprising, in a physiologically acceptable medium, at least one fatty phase comprising:

at least one non-volatile hydrocarbonated apolar oil, wherein the total amount of non-volatile hydrocarbonated apolar oil ranges from about 5% to about 30% by weight, relative to the total weight of the composition;

at least one non-volatile phenylated silicone oil chosen from trimethyl pentaphenyl trisiloxane, diphenylsiloxy phenyltrimethicone, or mixtures thereof, wherein the total amount of non-volatile phenylated silicone oil ranges from about 43% to 90% by weight relative to the total weight of the composition; and at least one wax, wherein the total amount of wax ranges from about 3% to about 30% by weight, relative to the total weight of the composition; and at least one volatile hydrocarbon oil, wherein the cosmetic composition is anhydrous, wherein the total amount of water is less than 1% by weight, relative to the total weight of the composition, and wherein the solid cosmetic composition is capable of providing improved color development and improved color transfer resistance.

17. The method according to claim 16, wherein the cosmetic composition is a solid composition having a hardness value ranging from about 60 and about 200 $Nm^{-1}$.

* * * * *

UNITED STATES PATENT AND TRADEMARK OFFICE
CERTIFICATE OF CORRECTION

PATENT NO. : 11,389,381 B2
APPLICATION NO. : 14/409146
DATED : July 19, 2022
INVENTOR(S) : Momoko Shimizu et al.

It is certified that error appears in the above-identified patent and that said Letters Patent is hereby corrected as shown below:

In the Claims

Claim 5, Column 48, Line 64, in Formula (III) third row of the formula, first occurrence, please delete the "2" after the "PH"; and Claim 5, Column 50, Line 43, please change "glmol" to -- g/mol --.

Signed and Sealed this
Twenty-seventh Day of August, 2024

Katherine Kelly Vidal
*Director of the United States Patent and Trademark Office*